United States Patent
Taguchi et al.

(10) Patent No.: US 9,514,550 B2
(45) Date of Patent: Dec. 6, 2016

(54) METHODS FOR MOTION COMPENSATED IMAGE RECONSTRUCTION AND SYSTEM RELATED THERETO

(75) Inventors: Katsuyuki Taguchi, Elkridge, MD (US); Hiroyuki Kudo, Tsukuba (JP)

(73) Assignee: The Johns Hopkins University, Baltimore, MD (US)

( * ) Notice: Subject to any disclaimer, the term of this patent is extended or adjusted under 35 U.S.C. 154(b) by 1133 days.

(21) Appl. No.: 12/452,089

(22) PCT Filed: Jun. 16, 2008

(86) PCT No.: PCT/US2008/007552
§ 371 (c)(1),
(2), (4) Date: Dec. 14, 2009

(87) PCT Pub. No.: WO2008/156764
PCT Pub. Date: Dec. 24, 2008

(65) Prior Publication Data
US 2010/0121183 A1    May 13, 2010

(51) Int. Cl.
*A61B 6/00* (2006.01)
*G06T 11/00* (2006.01)
*A61B 6/03* (2006.01)

(52) U.S. Cl.
CPC ........... *G06T 11/006* (2013.01); *A61B 6/5264* (2013.01); *A61B 6/03* (2013.01); *A61B 6/037* (2013.01); *G06T 2211/412* (2013.01)

(58) Field of Classification Search
CPC ...... A61B 6/5264; A61B 6/03; A61B 6/037; G06T 11/006
See application file for complete search history.

(56) References Cited

U.S. PATENT DOCUMENTS

2004/0136490 A1  7/2004  Edic et al.
2004/0267113 A1  12/2004  Thomson
2006/0002631 A1  1/2006  Fu et al.

*Primary Examiner* — Joseph M Santos Rodriguez
(74) *Attorney, Agent, or Firm* — Mintz Levin Cohn Ferris Glovsky and Popeo, P.C.; Peter F. Corless; Richard B. Emmons

(57) ABSTRACT

Featured are methods for reconstruction of images acquired from any of a number of scanning devices or apparatuses known to those skilled in the art which methods are established so as to provide a mechanism for compensating for motion of an object being imaged. Such methods of the present invention are such as to allow the clinician to select one or more specific methodologies that is appropriate for the expected motion, severity or complexity of the motion and efficient processing of projection data. Also feature are systems, apparatuses, software code and computer readable media which embody such methodologies.

12 Claims, 17 Drawing Sheets

Gating Window

Gating Window

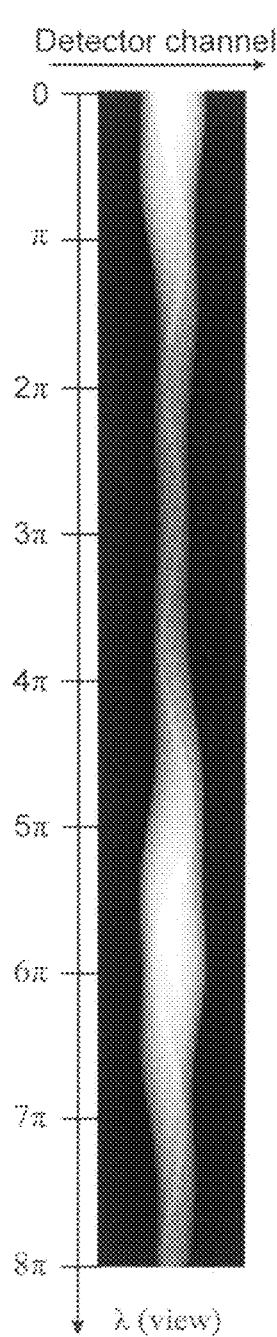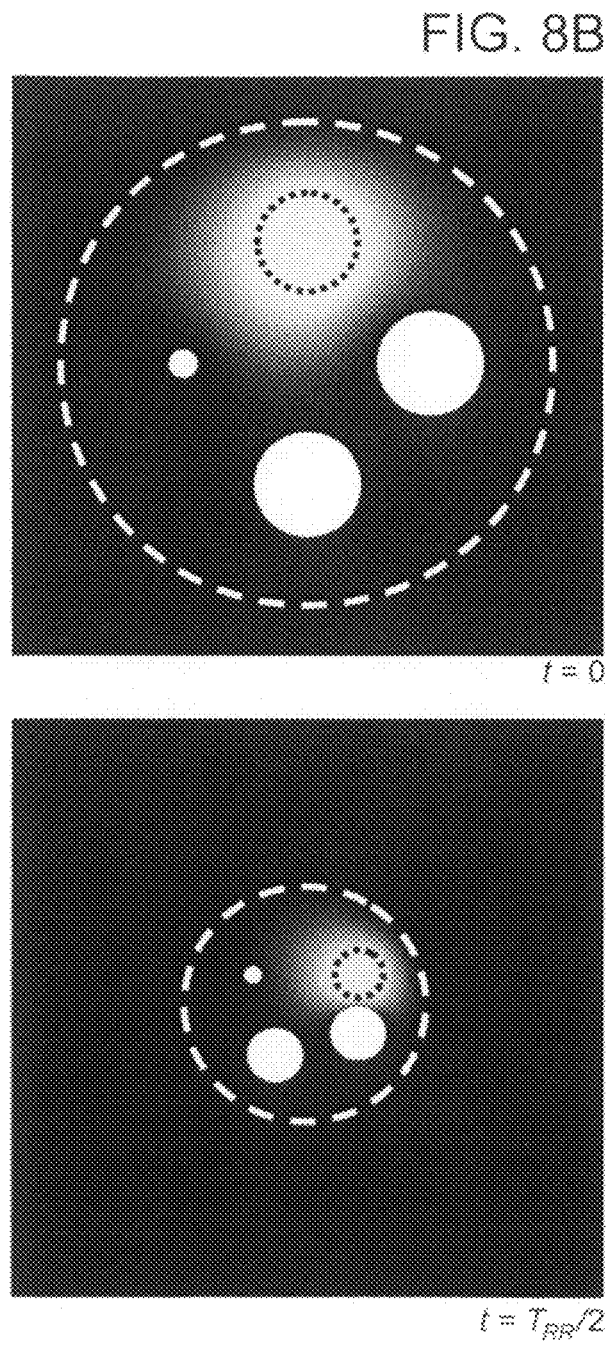
FIG. 8B
FIG. 8A
FIG. 8C

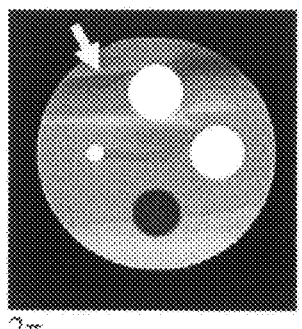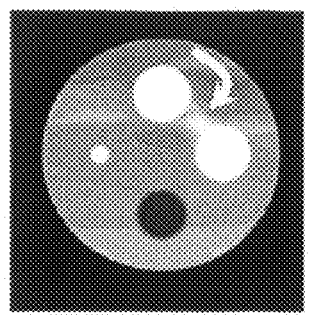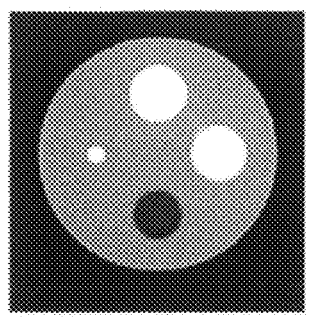
FIG. 11A  FIG. 11B  FIG. 11C
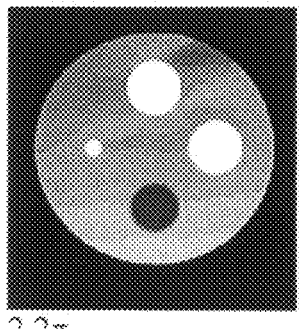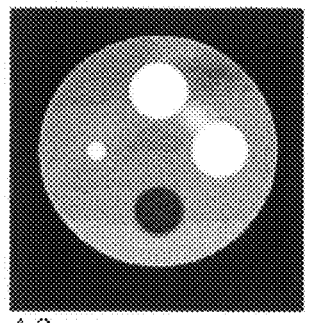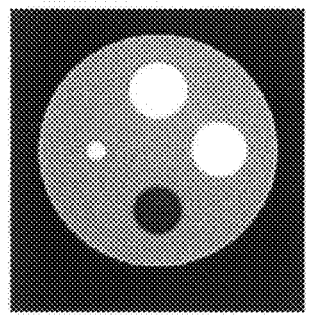
FIG. 11D  FIG. 11E  FIG. 11F
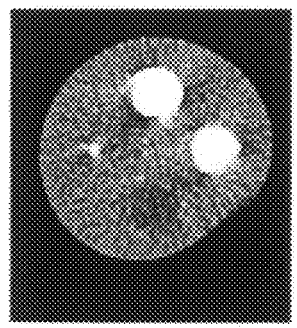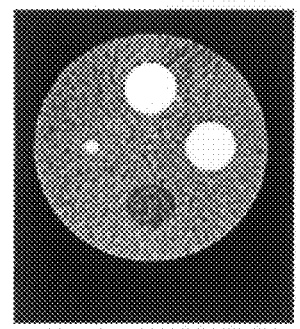
FIG. 12A  FIG. 12B
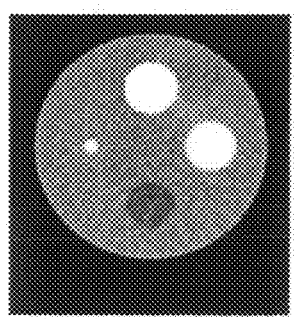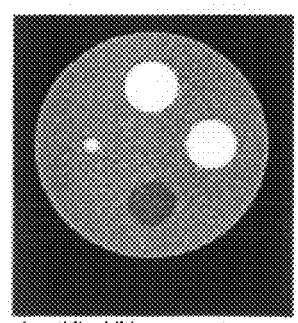
FIG. 12C  FIG. 12D

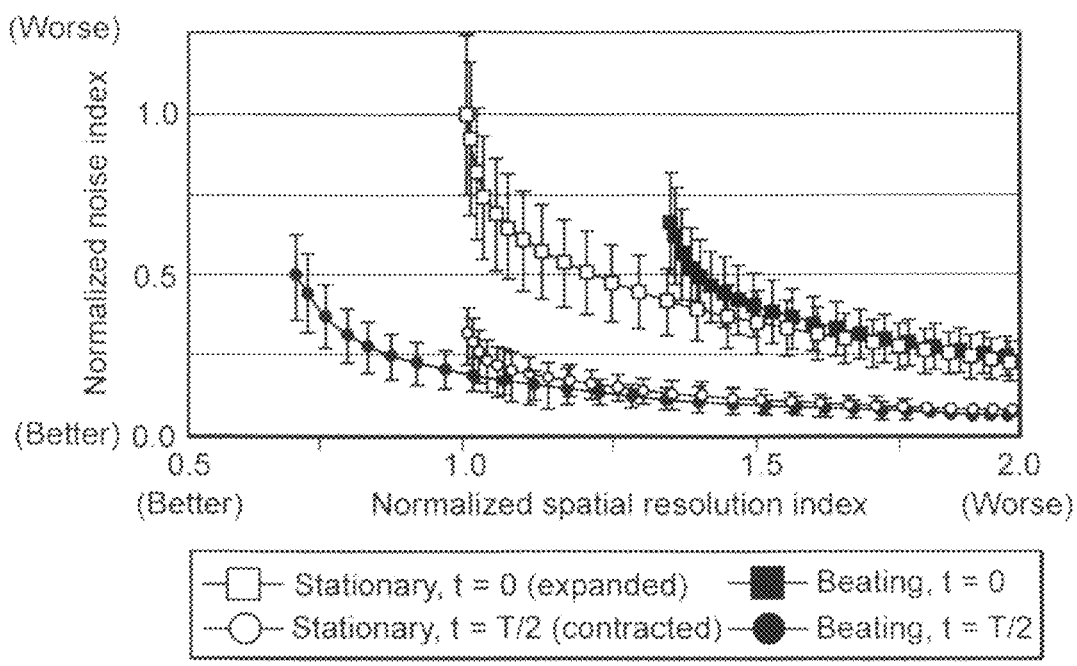
FIG. 13A
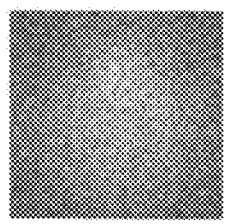
FIG. 13B
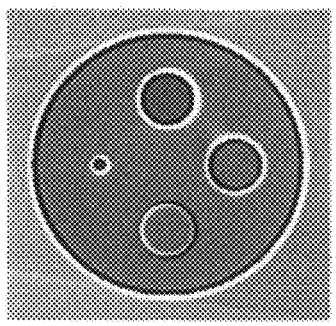 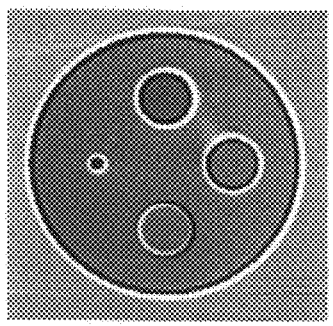 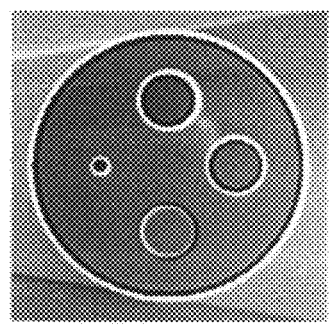
60 bpm, 6π      63 bpm, 6π      67 bpm, 6π
FIG. 14A      FIG. 14B      FIG. 14C

| Index | Center | Size | μ | Note |
|---|---|---|---|---|
| 1 | (0, 0) | 200 | 0.182 | muscle |
| 2 | (50, 0) | 40 | 0.276 | spine (north) |
| 3 | (0, 50) | 40 | 0.217 | iodine-blood |
| 4 | (-50, 0) | 40 | 0.175 | fat |
| 5 | (0, -50) | 5 | 0.217 | iodine-blood |

The definition of 5-ball phantom. Numbers are in mm for the centers and sizes and in $cm^{-1}$ for linear attenuation coefficients μ.

METHODS FOR MOTION COMPENSATED IMAGE RECONSTRUCTION AND SYSTEM RELATED THERETO

This application is a National Stage Filing of PCT Application No. PCT/US2008/007552, filed Jun. 16, 2008, which application claims the benefit of U.S. Provisional Application Ser. No. 60/934,719 filed Jun. 15, 2007 and U.S. Provisional Application Ser. No. 61/128,108 filed May 19, 2008, the teachings of all being incorporated herein by reference.

FIELD OF INVENTION

The present invention generally relates to methods, systems and apparatuses for reconstruction of an image(s) from acquired projection data, more particularly to methods, systems and apparatuses for reconstruction of an image(s) from acquired projection data while compensating for motion of the tissue or sample being imaged and more specifically relates to methods, systems and apparatuses for reconstruction of an image(s) from acquired projection data while compensating for motion of the tissue or sample being imaged, where the projection data is acquired using x-ray CT scanners, MRI scanners or systems/apparatuses embodying other nuclear medicine scanning or imaging techniques such as, for example, SPECT and PET.

BACKGROUND OF THE INVENTION

Cardiovascular disease remains the leading cause of death in the western world, placing an ever-increasing burden on both private and public health services ["The burden of chronic diseases and their risk factors: National and state perspectives," National center for chronic disease prevention and health promotion, Department of health and human services, Atlanta, Ga. February 2004]. The electrocardiogram-gated cardiac x-ray computed tomography (CT) imaging is a promising non-invasive technique for early detection and characterization of various signs of cardiac diseases such as fatty vulnerable soft plaque (atherosclerosis) in coronary arteries, perfusion defect in myocardial, etc [M. Gilard, J.-C. Cornily, P.-Y. Pennec, C. Joret, G. Le Gal, J. Mansourati, J.-J. Blanc, and J. Boschat, "Accuracy of Multislice Computed Tomography in the Preoperative Assessment of Coronary Disease in Patients With Aortic Valve Stenosis," *Journal of the American College of Cardiology*, vol. 47, pp. 2020-2024, 2006].

There are, however, two major problems with the current cardiac technique: large radiation dose to patients and insufficient temporal resolution [K. Taguchi, W. P. Segars, G. S. K. Fung, and B. M. W. Tsui, "Toward time resolved 4D cardiac CT imaging with patient dose reduction: estimating the global heart motion," in *Medical Imaging* 2006: *Physics of Medical Imaging*, San Diego, Calif., USA, 2006, pp. 61420J-9]. The typical radiation dose with cardiac CT is 10-15 mSv, which is 3-5 times as large as a standard chest CT scan. The current temporal resolution is merely 80-165 ms in contrast to the minimum requirement of 10-30 ms to observe the beating heart motion without motion artifact.

The current technique uses the electrocardiogram signals to select projection data acquired in a time or gating window that is placed within a cardiac cycle with relatively slow motion (e.g., mid-diastole). Images are then reconstructed by neglecting the cardiac motion within the time window, however, neglecting cardiac motion can result in blurring and artifacts in the reconstructed images. Also, this technique uses only 10-30% of the acquired projection data—the data within the cardiac time window—and throws away the rest of "off-phase" data, resulting in unnecessary radiation dose to patient if the tube current is not prospectively modulated.

A graphical representation of the current technique where a gating window is placed within a cardiac cycle (i.e., heart motion) is illustrated in FIGS. 1A, B. A graphical representation of image noise versus spatial/temporal resolution that show qualitatively that with this technique there is a trade-off made between noise and resolution is shown in FIGS. 2A, B. When the gating window is set as shown in FIG. 1A to have a relatively short duration (e.g., approximately 100 ms) with respect to the cardiac cycle, the spatial/temporal resolution is considered better, however, the image noise becomes a greater factor with regards to the graininess or sharpness of the image. If the duration of the gating window is set as illustrated in FIG. 1B so as to have a relatively long duration (e.g., approximately 300 ms) with respect to the cardiac cycle, then as shown in FIG. 2B, the spatial/temporal resolution becomes worse and image noise is less of a factor with regards to the graininess or sharpness of the image.

From the standpoint of reducing dosage, recently, a method to turn off the x-ray for the off-phase has been proposed [J. Hsieh, J. Londt, M. Vass, J. Li, X. Tang, and D. Okerlund, "Step-and-shoot data acquisition and reconstruction for cardiac x-ray computed tomography," *Medical Physics*, vol. 33, pp. 4236-4248, 2006]. This method is expected to reduce the dose significantly; however, this is achieved at the expense of the functional (motion) information. IN this technique, the only projection data that would be acquired is that during the cardiac time window, which as indicated above would only represent a small percentage of the projection data which could be acquired during a complete cardiac cycle.

Image reconstruction of dynamically deforming objects from projection data and known time-dependent motion field is of interest for x-ray computed tomography (CT). Clinical applications include the imaging of the heart, lungs, and liver with the cardiac and respiratory motions. Most of the currently known methods used for x-ray CT combine a gating scheme and an analytical reconstruction method. The gating scheme, as described above, uses a gating window to extract projection data acquired within a narrow window width (e.g., 80-165 ms for cardiac imaging). The images are then reconstructed while neglecting the motion within the window width. As discussed above, these methods suffer from a tradeoff between the image noise and the spatial/temporal resolution. If the in-frame motion is not negligible, it results in motion artifacts or blurring in images. The use of a narrower gating window will improve both the temporal and spatial resolution; however, it will increase the image noise as the number of photons contributed to an image is decreased. Thus, it has been sought to develop fully four-dimensional reconstruction algorithms, which compensate the motion of the object during the reconstruction process.

Algorithms have been developed to reconstruct images of the dynamically deforming objects with known motion from projections. Crawford, et al., proposed an approximate FBP-type (ramp filtering-based) method to compensate for a special combination of translation and anisotropic scaling (expansion and contraction) for the respiratory motion [Crawford, C. R., et al., *Respiratory compensation in projection imaging using a magnification and displacement model*. Medical Imaging, IEEE Transactions on, 1996. 15(3): p. 327-332]. The algorithm was a ramp filtering (FBP) with a change of variables to take a global motion model into account. A few exact methods have been proposed which compensate the standard or relaxed affine transformations. Roux et al. [Roux, S., bastien, Desbat, L., Koenig, A, and Grangeat P, *Exact reconstruction in 2D dynamic CT: compensation of time-dependent affine deformations*. Physics in Medicine and Biology, 2004. 49(11): p. 2169-2182] developed an exact algorithm for a global time-dependent affine transformation by incorporating transformation operation into Noo's derivative Hilbert transform (DFBP) algorithm [Noo, F., et al., *Image reconstruction from fan-beam projections on less than a short scan*. Physics in Medicine and Biology, 2002. 47(14): p. 2525-2546].

Desbat, et al. extended Roux's motion model to a relaxed version of affine transformation [Desbat L., Roux S. and Grangeat P., *Compensation of Some Time Dependent Deformations in Tomography*, In: Noo F, Zeng G L, Kudo F editors, The $8^{th}$ International meeting on fully three-dimensional image reconstruction in Radiology and Nuclear Medicine, 2005 Jul. 6-9, 2005, Salt Lake City, Utah; 2005, P. 120-32]. In these methods, the DFBP or DBPF algorithms were developed for stationary objects. With all of these methods, the image reconstruction formulae integrate the compensation of the used motion model.

Such DFBP-based affine transformation compensation algorithms DAFBP, are exact; however, the motion model is restricted such that lines (rays) remain lines even after deformation. Most of the non-rigid transforms such as respiratory or cardiac motion do not satisfy this restriction, i.e., lines become curves with deformation. For respiratory compensation, Ritchie et al. [Ritchie C J, Crawford C R, Godwin J D, King K F, Yongmin K, Correction of computed tomography motion artifacts using pixel-specific backprojection Medical imaging, IEEE Transactions on 1996; 15(3): 333-42] applied Crawford's algorithm on a local basis by changing the motion model for each pixel. Despite its global nature of the ramp filtering, the reconstructed images were in good quality demonstrating significantly reduced motion artifact.

Schafer, et al., also have proposed an empirical FBP-based method which, during the backprojection process, merely traces the motion of a point of reconstruction and select the corresponding ray passing through the point at each time t [Schafer, D., et al., *Motion-compensated and gated cone beam filtered back-projection for 3-D rotational X-ray angiography*. Medical Imaging, IEEE Transactions on, 2006. 25(7): p. 898-906.]. Schafer's method is based on so called direct cone-beam geometry for C-arm cardiac imaging, which has been extended to parallel-fan-beam geometry for helical cardiac CT imaging and showed promises [van Stevendaal, U., et al. *Motion-compensated reconstruction in helical cardiac CT. in the 9th international conference on fully three-dimensional reconstruction in radiology and nuclear medicine.* 2007. Lindau, Germany]. An image reconstructed by Schafer's method with wider gating window width (40% of the R-R interval) exhibited less motion artifact with improved sharpness than an image reconstructed by the conventional FBP method with narrower window width (22%). Schafer's method has intuitively been understood as a crude approximation.

It thus is desirable to provide new methodologies or techniques for reconstructing projection data while compensating for motion of object(s) within the field of view of the scanning or imaging apparatus. It also would be desirable for such methodologies or techniques to be adapted for use in combination with any of a number of imaging modalities as known to those skilled in the art as well as being adapted for use in reconstructing images for a wide range of items including biological tissue (e.g., hearts, livers, respiratory, muscuskeletal, brain imaging with a length scan) and non-distractive industrial scanning. It also would be desirable to provide systems, apparatuses, software code and computer readable mediums embodying such software code that embody such methodologies and techniques

SUMMARY OF THE INVENTION

The present invention features methods for reconstruction of images acquired from any of a number of scanning devices or apparatuses known to those skilled in the art which methods are established so as to provide a mechanism for compensating for motion of an object being imaged. Such methods of the present invention are such as to allow the clinician to select one or more specific methodologies that is appropriate for the expected motion, severity or complexity of the motion and efficient processing of projection data. Also feature are systems, apparatuses, software code and computer readable media which embody such methodologies.

The methodologies of the present invention also are advantageous as they are easily adaptable for use with any of a number of tomographic imaging modalities known to those skilled in the art. Such imaging modalities include, but are not limited to: x-ray scanners, such as CT scanners, and Magnetic Resonance Imaging scanners as well as apparatuses/systems embodying other nuclear medicine imaging or scanning techniques such as for example, SPECT and PET. It should be noted that for convenience as well as simplifying the discussion, the discussion in the subject application generally refers to x-ray CT scanning; however, this shall not be construed as limiting the invention to only this imaging modality.

In one aspect, the present invention features a methodology for reconstructing acquired projection data, that includes selecting a given image reconstruction methodology based at least on expected motion of the object to be imaged and reconstructing an image from the acquired projection data using the selected methodology. In further embodiments, such methods further include estimating a motion vector filed for the object being imaged and wherein the image reconstruction methodology is established so as to utilize the estimated motion vector field to compensate for motion of the object when reconstructing the image.

In yet further embodiments, such methods include optimizing the reconstructed image. Such optimizing includes iteratively comparing projection data (i.e., calculated projection data) determined from a reconstructed image with acquired projection data and determining that a given reconstructed image is optimal when such comparison shows a convergence of the determined projection data with the acquired projection data. In yet further embodiments such iterative comparing includes determining if there is a convergence of such data and in the case where it is determined that there is not convergence, modifying the motion vector field that was used in the prior reconstruction step and reconstructing another image and then comparing the determined projection data from the another reconstructed image with the acquired projection data. The foregoing process is repeated until it is determined that there is a convergence, and in such a case the related reconstructed image is determined to be optimal.

In yet further embodiments, the reconstructing of projection data further includes providing a reconstructing algorithm that is appropriate for the reconstruction of projection data. In further embodiments such providing includes providing a reconstructing algorithm being selected from the group consisting of a DABPF algorithm, a $DA_xBPF$ algorithm and a $FBP_x$ algorithm. In further embodiments, such providing includes determining the complexity of motion of the object being imaged and selecting an algorithm appropriate for the level of complexity. In further embodiments, such providing further includes assessing the required efficiency of image reconstruction and selecting an algorithm appropriate for the required efficiency. In further embodiments, such selecting is based on efficiency and motion complexity.

In another aspect of the present invention, there is featured a methodology for reconstructing acquired projection data, that reconstructing an image from the acquired projection data using a given methodology that is appropriate for reconstructing an image including an object having an expected motion. In further embodiments, the methodology is appropriate for one or both of the complexity of motion of the object and the required efficiency of image reconstruction. In further embodiments, such methods further include estimating a motion vector filed for the object being imaged and wherein the image reconstruction methodology is established so as to utilize the estimated motion vector field to compensate for motion of the object when reconstructing the image.

In yet further embodiments, such methods include optimizing the reconstructed image. Such optimizing includes iteratively comparing projection data determined or calculated from a reconstructed image with acquired projection data and determining that a given reconstructed image is optimal when such comparison shows a convergence of the determined projection data with the acquired projection data. In yet further embodiments such iterative comparing includes determining if there is a convergence of such data and in the case where it is determined that there is not convergence, modifying the motion vector field that was used in the prior reconstruction step and reconstructing another image and then comparing the determined projection data from the another reconstructed image with the acquired projection data. The foregoing process is repeated until it is determined that there is a convergence, and in such a case the related reconstructed image is determined to be optimal.

In yet further embodiments, the reconstruction of projection data further includes providing a reconstructing algorithm that is appropriate for the reconstructing of projection data. In further embodiments such providing includes providing a reconstructing algorithm being selected from the group consisting of a DABPF algorithm, a $DA_xBPF$ algorithm and a $FBP_x$ algorithm. In further embodiments, such providing includes determining the complexity of motion of the object being imaged and selecting an algorithm appropriate for the level of complexity. In further embodiments, such providing further includes assessing the required efficiency of image reconstruction and selecting an algorithm appropriate for the required efficiency. In further embodiments, such selecting is based on efficiency and motion complexity.

In yet further embodiments, such methods further includes diagnostically evaluating the reconstructed image and assessing need for medical treatment. In case such medical treatment is determined to be needed, such methods further include determining an appropriate course of treatment, such as for example, surgical procedures, or a course of drug treatment and/or physically therapy.

Also featured are a system, device or apparatus embodying one or more of the methodologies of the present invention. Also featured is a computer software program for execution on a computer and a computer readable medium including such a software program which software program embodies one or more methodologies of the present invention.

Other aspects and embodiments of the invention are discussed below.

DEFINITIONS

The instant invention is most clearly understood with reference to the following definitions:

A computer readable medium shall be understood to mean any article of manufacture that contains data that can be read by a computer or a carrier wave signal carrying data that can be read by a computer. Such computer readable media includes but is not limited to magnetic media, such as a floppy disk, a flexible disk, a hard disk, reel-to-reel tape, cartridge tape, cassette tape or cards; optical media such as CD-ROM and writeable compact disc; magneto-optical media in disc, tape or card form; paper media, such as punched cards and paper tape; or on carrier wave signal received through a network, wireless network or modem, including radio-frequency signals and infrared signals.

MRI shall be understood to mean magnetic resonance imaging (also sometimes referred to as Nuclear Magnetic Resonance Imaging—NMRI), and generally describes and imaging technique that involves the transmission of radio-frequency (RF) magnetic fields into a specimen (e.g., the patient's body) while the specimen is subjected to a strong static magnetic field, wherein the RF magnetic field is tuned to excite the magnetic resonance frequency of a particular nuclear species of interest such as the nuclei of hydrogen (protons). The MRI/NMRI technique makes use of the fact that after the selected nuclei composing the specimen (e.g., hydrogen nuclei) are excited by the applied RF magnetic field, they "relax" back to equilibrium by emitting a RF magnetic field at the same frequency. The nucleus most commonly employed in magnetic resonance is the proton in the hydrogen atom, because the hydrogen nucleus has the largest magnetic moment for its spin, has the highest concentration in the body, and thus provides the strongest resonance signals. Other nuclei used include but are not limited to those of phosphorus (phosphorus-31), carbon-13, oxygen-17 and fluorine (fluorine-19). A computer analyzes the emissions from, for example, the hydrogen nuclei of water molecules in body tissues and constructs images of anatomic structures based on the concentrations of such nuclei.

Projection data shall be understood to mean the data acquired using an x-ray CT scanning process, however it also shall be understood to be inclusive of any data acquired from the use of a given scanning modality and also shall be understood to include the specific terminology used for a given imaging modality for such data such as for example acquired image data for an MRI scanning process.

PET shall be understood to mean positron emission tomography and generally describes a medical imaging technique that detects the gamma rays produced by positrons emitted from injected radionuclides. In this technique, a very small amount of a radiolabeled compound is inhaled by or injected into the patient. The injected or inhaled compound accumulates in the tissue to be studied. As the radioactive atoms in the compound decay, they release smaller particles called positrons, which are positively charged. When a positron collides with an electron (negatively charged), they are both annihilated, and two photons (light particles) are emitted. The photons move in opposite directions and are picked up by the detector ring of the PET scanner. A computer uses this information to generate three-dimensional, cross-sectional images that represent the biological activity where the radiolabeled compound has accumulated. The Tomographic images are formed by computer analysis of the photons detected from annihilation of the positrons; the images, often quantitated with a colour scale, show the uptake and distribution of the substances in the tissue, permitting analysis and localization of metabolic and physiological function.

SPECT (or less commonly, SPET) shall be understood to mean single photon emission computed tomography and generally describes a nuclear medicine tomographic imaging technique using gamma rays. In this technique a small amount of a radioactive drug is injected into a vein and a scanner is used to make detailed images of areas inside the body where the radioactive material is taken up by the cells. Imaging is performed by using a gamma camera to acquire multiple 2-D images (also called projections), from multiple angles. A computer is then used to apply a tomographic reconstruction algorithm to the multiple projections, yielding a 3-D dataset. This dataset may then be manipulated to show thin slices along any chosen axis of the body, similar to those obtained from other tomographic techniques, such as MRI, CT, and PET. To acquire SPECT images, the gamma camera is rotated around the patient. Projections are acquired at defined points during the rotation, typically every 3-6 degrees. In most cases, a full 360 degree rotation is used to obtain an optimal reconstruction.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein:

FIGS. 2A, B generally correspond to the gating window arrangement shown in FIGS. 1A, B respectively.

FIGS. 8(a)-8(c) are illustrative views of sonogram cf 5-ball phantom 63 bpm (FIG. 8(a)) and of two affine transform (FIGS. 8(b)-8(c)).

FIGS. 11(a)-11(f) are various illustrative views of images reconstructed with various angular ranges.

FIGS. 12(a)-12(d) are illustrative views of images reconstructed from noisy projections.

FIGS. 13(a)-13(b) provide a graphical view of noise-resolution tradeoff curves (13(a)) and an illustrative view of an s.d. mapping (13(b)) obtained from a beating heart.

FIGS. 14(a)-(c) are illustrative views of difference images.

(FIG. 21(a)) rotation, (FIG. 21(b)) scaling, (FIG. 21(c)) translation, and (FIG. 21(d)) all of rotation, scaling, and translation are involved. Two object motion speeds for each condition were simulated. Images were reconstructed by either FBP with halfscan weight, Schafer's method with a uniform weight over 3 rotations, or FBPx with a uniform weight over 3 rotations.

DESCRIPTION OF THE PREFERRED EMBODIMENT

Methods of the present invention are generally directed to the reconstruction of images from projection data acquired using any of a number of scanning devices or apparatuses known to those skilled in the art and more particularly to methods that are established so as to provide a mechanism for compensating for motion of an object being imaged, using such devices or apparatuses. More specifically, the scanning methodologies include any of a number of modalities embodying tomography imaging. As described further herein, such methods provide a mechanism by which the clinician or technician can select one or more specific methodologies that is appropriate for the expected motion, severity or complexity of the motion and efficient processing of projection data. The present invention also includes systems, apparatuses, software code and computer readable media which embody such methodologies for reconstruction of an image from the acquired projection data.

As also described herein, the methodologies of the present invention are particularly advantageous as they are easily adaptable for use with any of a number of tomographic imaging modalities known to those skilled in the art. Such imaging modalities include, but are not limited to: x-ray scanners, such as CT scanners, and Magnetic Resonance Imaging scanners as well as systems/apparatuses embodying other nuclear medicine imaging/scanning techniques including SPECT and PET. It should be noted that for convenience as well as simplifying the discussion, the discussion in the subject application generally refers to x-ray CT scanning; however, this shall not be construed as limiting the invention to only this imaging modality.

Figure 3A:
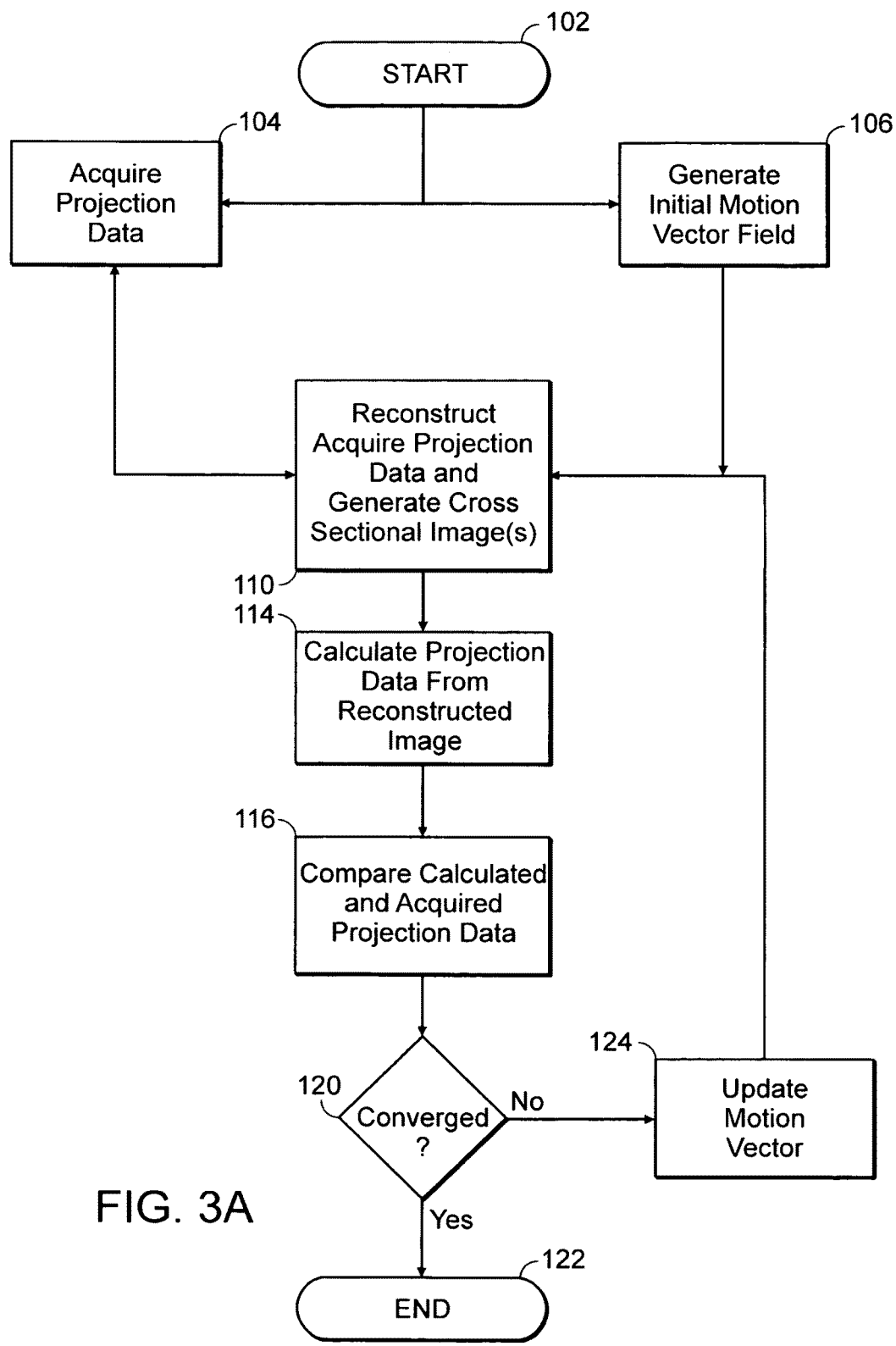
FIGS. 3A-B are high level flow diagram illustrating various processes for motion compensated reconstruction of images according to the present invention.

Referring now to the various figures of the drawing wherein like reference characters refer to like parts, there is shown in FIGS. 3A, B high level flow diagrams that illustrate various methodologies for reconstructing images according to the present invention. The flow charts herein illustrate the structure of the logic of the different methodologies/inventions, which can be embodied in computer program software for execution on a computer, digital processor or microprocessor. Those skilled in the art will appreciate that the flow charts illustrate the structures of the computer program code elements, including logic circuits on an integrated circuit, that function according to the present inventions. As such, the present inventions are practiced in its essential embodiments by a machine component that renders the program code elements in a form that instructs a digital processing apparatus (e.g., computer) to perform a sequence of function step(s) corresponding to those shown in the flow diagrams.

Referring now to FIGS. 3A, B wherein like reference characters refer to like parts/method steps, there are shown flow-diagrams that illustrates two aspect or embodiments of the present invention for reconstructing images while compensating for motion in the volume or area being imaged. To start the imaging process, the clinician or technician prepares the object or person to be imaged so that the area or volume of interest is located in the field of view of the imaging/scanning device or apparatus, Step 102. For example, most scanning or imaging devices or apparatuses include a moveable table so that a person can lie down on the table or the object placed on the table and then moved into the scanning device/apparatus. Thus, it is understood that those preliminary actions or steps necessary to carry out the imaging process are performed as part of the starting of the process.

After the imaging process is started (e.g., the table is moved and it is positioned so the scanning process can be started), the clinician or technician initiates the scanning process for the given imaging modality and projection data is thereafter acquired, Step 104. It should be recognized that projection data acquisition is performed according to the usually and customary manner for the given modality. For example, the projection data for an entire volume of interest can be acquired before the reconstruction process is started. Also, for example projection data acquired using the CT scan process usually involves moving the table with respect to the CT scanner during the scanning process so that projection data of the desired volume is obtained.

Before starting the process for reconstructing the projection data, the clinician or technician also generates an initial motion vector field, Step 104, using any of a number of techniques or methods known to those skilled that provides an time-dependent estimation of motion. In an exemplary embodiment, such techniques/methods include an image-based time dependent 2D motion estimation method comprising the steps of (a) reconstructing cine images, (b) find "quiet" motion phases (e.g., end-systole, mid diastole), (c) initialize the motion vector field; (d) warp the images at the quiet phases (d) evaluate convergence and (e) update the motion vector field until the evaluation determines that the vector field has converged. Convergence is considered to be found when the comparison reflects a minimally difference. In an ideal situation, the difference result would be at or about zero. Descriptions of other methods or techniques for creating a motion vector field are found in van Stevendaal, U., et al. *Motion-compensated reconstruction in helical cardiac CT.* in *the 9th international conference on fully three-dimensional reconstruction in radiology and nuclear medicine.* 2007. Lindau, Germany; Desbat, L., S. Roux, and P. Grangeat, *Compensation of Some Time Dependent Deformations in Tomography* Medical Imaging, IEEE Transactions on, 2007. 26(2): p. 261-269; Roux, S., et al., *Exact reconstruction in 2D dynamic CT: compensation of time-dependent affine deformations.* Physics in Medicine and Biology, 2004. 49(11): p. 2169-2182; and Ritchie C J, Crawford C R, Godwin J D, King K F, Yongmin K, Correction of computed tomography motion artifacts using pixel-specific backprojection Medical imaging, IEEE Transactions on 1996; 15(3): 333-42. The foregoing are exemplary and thus it is within the scope of the present invention to use any technique or methodology for creating or generating a motion vector field now known or hereinafter developed.

Figure 3B:
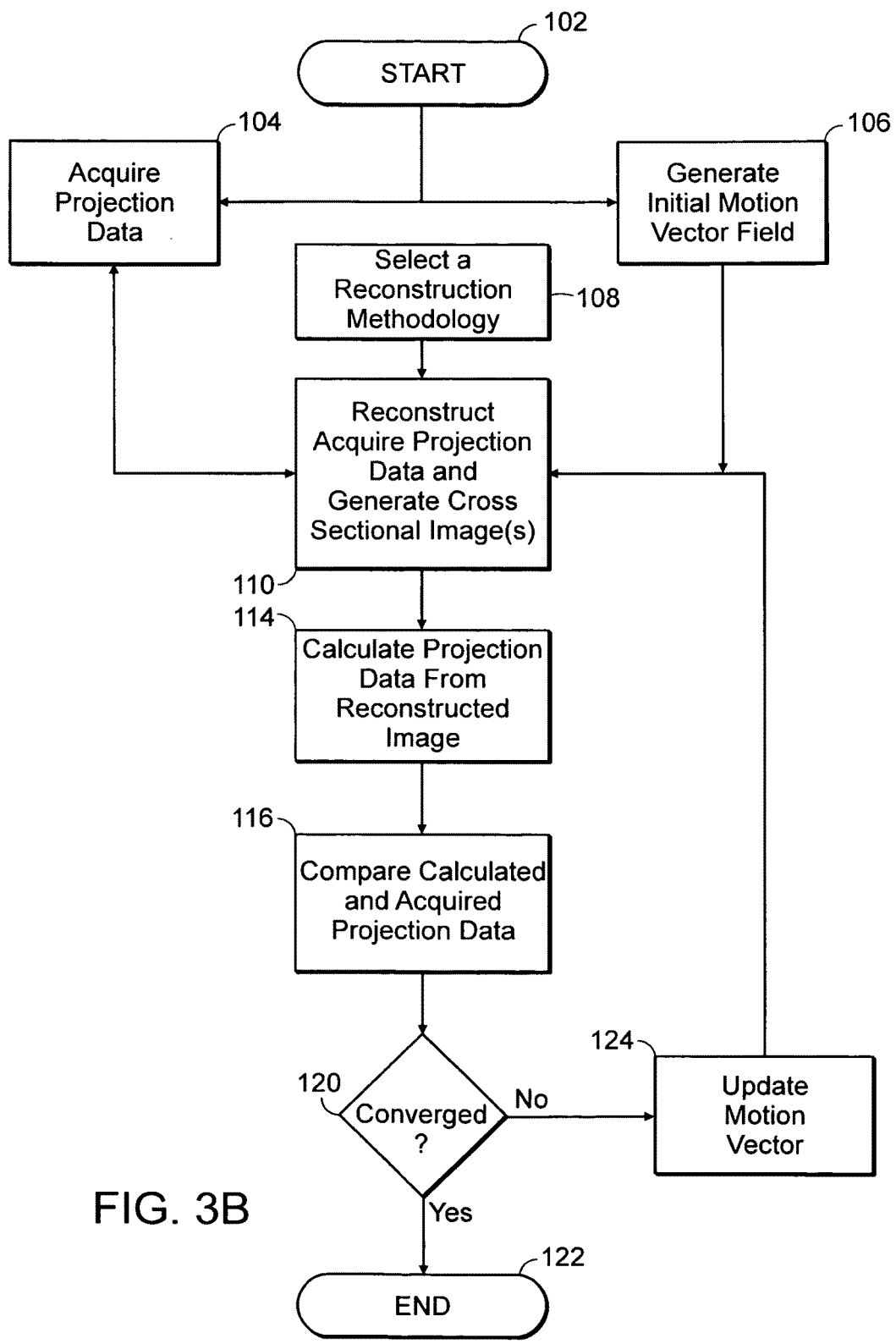

As shown more specifically in FIG. 3B, in the second aspect or embodiment of the present invention before reconstruction the projection data while compensating for motion, the clinician or technician selects a particular reconstruction methodology or reconstruction algorithm that is appropriate for the region of interest, Step 108. In further embodiments, such selection includes evaluating, inter alia, the complexity of the motion to be dealt with and/or efficiency of the processing of the projection data.

As described hereinafter, the present invention features a plurality of different reconstruction methodologies that, for example, each have different capabilities for dealing with motion that may be present in the volume or slice being imaged and different levels of computational needs to process the projection data and the motion vector field information so as to yield a reconstructed image. Thus, depending upon a desired speed or efficiency for processing the data and/or the complexity of the motion a clinician or technician selects the reconstruction methodology that has the desired capabilities. In more particular embodiments, the clinician or technician utilizes the motion vector field generated or created in Step 106 to assist in making such a determination.

In yet more particular embodiments, such selecting a methodology include selecting a reconstructing algorithm that is appropriate for reconstructing the projection data. In more specific embodiments, such selecting a reconstructing algorithm includes selecting a reconstructing algorithm from the group consisting of a DABPF algorithm, a $DA_xBPF$ algorithm and a $FBP_x$ algorithm.

After acquiring the projection data and generating an initial motion vector field (FIGS. 3A, B Steps 104, 106) and in the case of FIG. 3B, also after selecting a reconstructing methodology (Step 108), the process continues with the reconstruction of the projection data so that an image of the volume or slice being imaged can be created from the inputted acquired projection data and the generated initial motion vector field, Step 110. More particularly, in this step cross-sectional image(s) are re-constructed from the acquired projection data using the current estimate of the motion field vector.

In yet more particular embodiments, the reconstructing methodology embodies a given reconstructing algorithm that is appropriate for reconstructing the projection data. In more specific embodiments, such reconstructing algorithms include a DABPF algorithm, a DA$_x$BPF algorithm and a FBP$_x$ algorithm. These different algorithms are described hereinafter.

In further embodiments, the methods of the present invention also include optimizing the reconstructed image by assessing the divergence if any between the acquired projection data and projection data calculated using a reconstructed image. After generating the cross-sectional image(s), Step 110, using any of a number of techniques known to those skilled in the imaging arts, projection data is calculated, Step 114. As is known to those skilled in the art, there are a number of processes or techniques that allow one to take the cross-sectional image(s) generated in Step 110 and calculate projection data that if had been acquired would have yielded an image corresponding to the reconstructed cross-sectional image(s). The projection data being calculated is in the form it would have been for the imaging modality used to acquire the projection data in Step 104.

After generating the calculated projection data, a comparison is made with the acquired projection data that corresponds to the re-constructed slice or reconstructed image, Step 116, and a determination is made to determine if a convergence is shown, Step 120. Such comparison and determining provides a mechanism to determine analytically if the reconstructed image should be is a good or accurate representation of the image area or volume that had been imaged. If it is concluded that the reconstructed image should be or is a good or accurate representation of the image area or volume that had been imaged, then it is determined that the projection data has converged (Yes, Step 120) and the image reconstruction process is ended, Step 122.

If it is concluded that the reconstructed image would not be or is not a good or accurate representation of the area or volume that had been imaged, then it is determined that the projection data has not converged (No, Step 120) and the logic flow proceeds to Step 124, whereat the motion vector filed is updated or modified, Step 124, using any of a number of techniques known to those skilled in the art. The logic flow then proceeds to Step 110 and another cross-sectional image(s) is reconstructed from the projection data using the updated motion vector field. The logic flow than continues with Steps 114, 116, and 120 to determine convergence. If convergence is not found, then the above process is repeated until convergence is found or the process times out.

Convergence in connection with the optimization process is determined to be present when the difference between the acquired projection data and the calculated projection data or the parameter used to represent such a difference is determined to be minimal. For example, the minimal value would be at a or about a valley or similar position as shown from a plot of the differences.

It should be recognized that while the optimization process is described and shown as a serial process, this shall not be limiting as the optimization process or portions of the illustrated process can be performed as an iterative process so as to generate a plurality of comparisons which are then later evaluated to determine if there is convergence.

The following describes the different reconstruction algorithms of the present invention.

DABPF & DAxBPF Algorithms

Hereinafter, first a rigid motion is discussed and a basic algorithm, DABPF is derived and then DAxBPF is outlined (i.e., how to apply DABPF on a local basis to compensate for non-rigid motion). There then follows sections regarding present schemes and results of computer simulations, discussion and conclusion.

DABPF

In the following, an exact algorithm, DABPF, is derived from DBPF algorithm to reconstruct a dynamic object with globally defined time-dependent affine transformation.

Notations:

The right hand coordinate system with x=(x,y) is used and the time-dependent two-dimensional deforming object is defined by $f_0(x_0)$, $x_0 \in R^2$, at the reference time $t=t_0$, and $f_t(x_t)$, $x_t \in R^2$, at time t. The time-dependent affine operation $\Gamma_t$ projects a point $x_t$ at time t to a point $x_0$ at time $t_0$:

$$\Gamma_t(x_t) = A_t x_t + B_t = x_0, \quad (1)$$

where $$A_t = \begin{bmatrix} a_{11}(t) & a_{12}(t) \\ a_{21}(t) & a_{22}(t) \end{bmatrix} \text{ and } B_t = \begin{bmatrix} B_1(t) \\ B_2(t) \end{bmatrix}. \quad (2)$$

It is suppose that this affine deformation is invertible, that is, $\forall t$, $\det A_t \neq 0$, where $\det A_t$ is the determinant of matrix $A_t$. The object can thus be written as $$f_t(x_t) = f_0(\Gamma_t(x_t)) = f_0(x_0). \quad (3)$$

The true circular source trajectory $s_t(\lambda)$ and fan-beam projections $g_t(\lambda, \alpha_t)$ can be noted as:

$$s_t(\lambda) = (-R_s \cos \lambda, -R_s \sin \lambda)^T, \quad (4)$$

$$g_t(\lambda, \alpha_t) = \int_0^\infty f_t(s_t(\lambda) + l\alpha_t) dl \quad (5)$$

where $\lambda \in R$ is a parameter of the source trajectory, $\alpha_t$ is a unit vector along a ray from $s_t(\lambda)$, and $R_s$ is the distance from the source to the rotation axis. Note $\lambda$ is monotonically increasing function of time, for example, $$\lambda = \omega t. \quad (6)$$

DABPF Algorithm

Figure 1A:
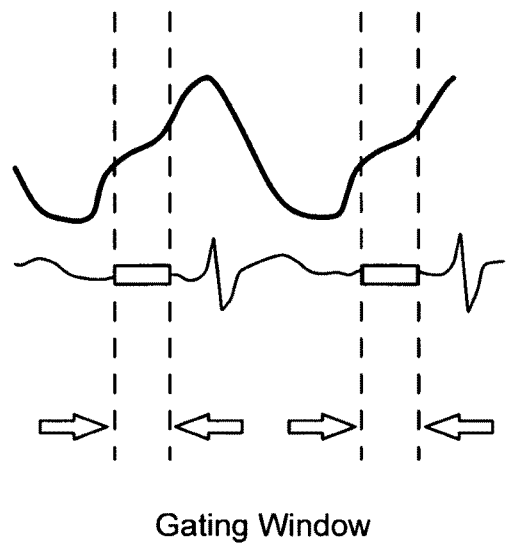
FIGS. 1A, B are graphical representations of a conventional technique illustrating placement of the gating window within a cardiac cycle (i.e., heart motion).
Figure 1B:
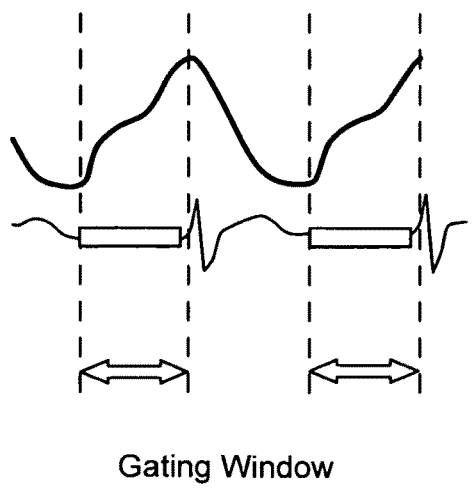
Figure 2A:
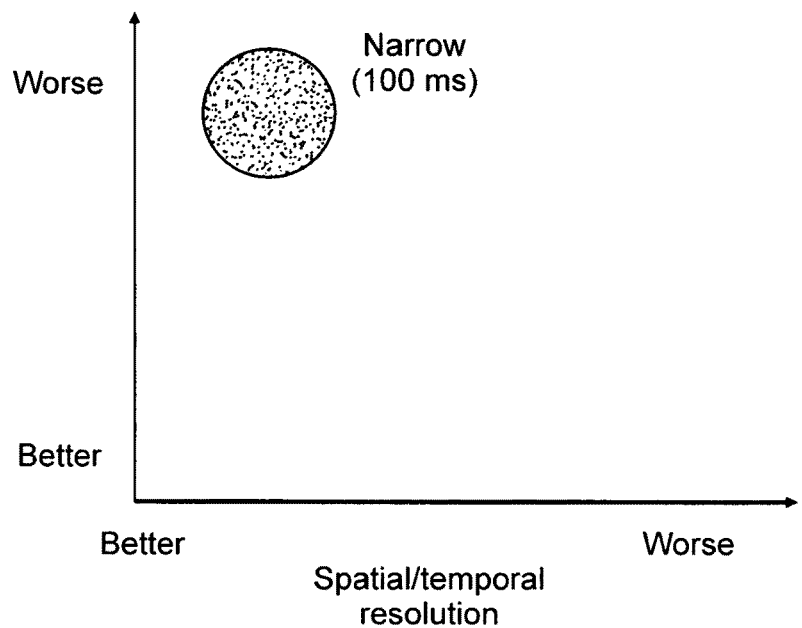
FIGS. 2A, B are graphical representations of image noise versus spatial/temporal resolution that show qualitatively illustrating the trade-off made between noise and resolution.
Figure 2B:
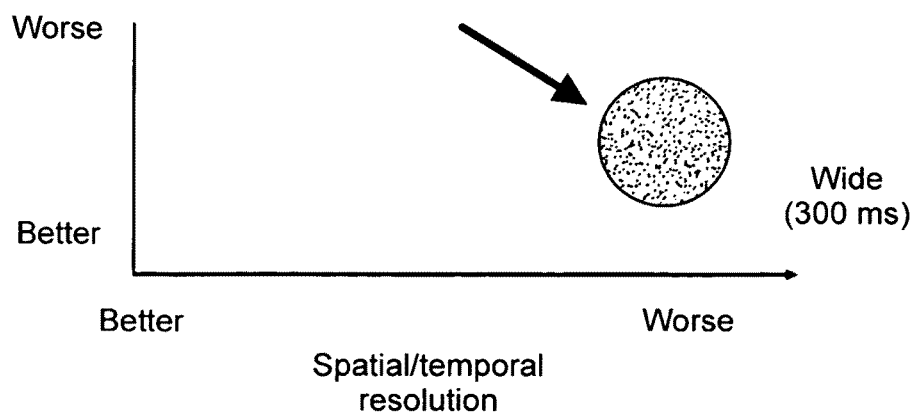

Let a 2D function $b_{0,\theta}(x_0)$ be a Hilbert transformed 2D image $f_0(x_0)$ at the reference time $t_0$, where $\theta$ is a unit vector that defines the direction of 1-D finite inverse Hilbert transform [F. Noo, R. Clackdoyle, and J. D. Pack, "A two-step Hilbert transform method for 2D image reconstruction," *Physics in Medicine and Biology*, vol. 49, pp. 3903-3923, 2004] (see also Appendix). First $b_{0,\theta}(x_0)$ is obtained from measured projections $g_t(\lambda, \alpha_t)$. A circular source orbit $s_t(x_0)$ around the object f, is transformed into a virtual source trajectory $s_0(\lambda)$ around the object $f_0$ at $t_0$ (FIG. 1):

$$s_0(\lambda) = \Gamma_t(s_t(\lambda)). \quad (7)$$

The projection data with the virtual path can then be obtained by $$g_0(\lambda, \alpha_0) = \|A_t \alpha_t\| g_t(\lambda, \alpha_t), \quad (8)$$

where $$\alpha_0 = A_t \alpha_t / \|A_t \alpha_t\|. \quad (9)$$

Proof:

Using Eq. (3) inside the integral of the right hand side of Eq. (5) and the linearity, the object f at time t can be noted by $$f_t(s_t(\lambda) + l\alpha_t) = f_0(\Gamma_t[s_t(\lambda) + l\alpha_t]) \quad (10)$$

$$= f_0(\Gamma_t[s_t(\lambda)] + l \times \Gamma_t[\alpha_t - O_t])$$

$$= f_0(\Gamma_t[s_t(\lambda)] + l \times (A_t \alpha_t + B_t - B_t))$$

$$= f_0(s_0(\lambda) + l A_t \alpha_t).$$

Inserting Eq. (10) into Eq. (5) and changing a variable, $l=\hat{l}/\|A_t\alpha_t\|$, one gets $$g_t(\lambda, \alpha_t) = \int_0^\infty f_0(s_0(\lambda) + lA_t\alpha_t)dl \qquad (11)$$

$$= \frac{1}{\|A_t\alpha_t\|}\int_0^\infty f_0\left(s_0(\lambda) + \hat{l}\frac{A_t\alpha_t}{\|A_t\alpha_t\|}\right)d\hat{l}$$

$$= \frac{1}{\|A_t\alpha_t\|} \times \int_0^\infty f_0(s_0(\lambda) + \hat{l}\alpha_0)d\hat{l}$$

$$= \frac{1}{\|A_t\alpha_t\|} \times g_0(\lambda, \alpha_0),$$

where $\alpha_0$ is given by Eq. (9).

[Q.E.D.]

The derivative of the virtual projection data, Eq. (8), can then be calculated by using product rule and Eq. (6)

$$\frac{\partial}{\partial\lambda}g_0(\lambda, \alpha_0) = \frac{\partial}{\partial\lambda}\|A_t\alpha_t\|g_t(\lambda, \alpha_t) + \|A_t\alpha_t\|\frac{\partial}{\partial\lambda}g_t(\lambda, \alpha_t) = \qquad (12)$$

$$\frac{1}{\omega}\left\|\frac{\partial A_t}{\partial t}\alpha_t\right\|g_t(\lambda, \alpha_t) + \|A_t\alpha_t\|\frac{\partial}{\partial\lambda}g_t(\lambda, \alpha_t)$$

where $$\frac{\partial}{\partial\lambda}g_t(\lambda, \alpha_t) = \lim_{\varepsilon\to 0}\frac{g_t(\lambda + \varepsilon, \alpha_t) - g_t(\lambda, \alpha_t)}{\varepsilon}. \qquad (13)$$

The following procedures are the same as DBPF algorithms (see F. Noo, R. Clackdoyle, and J. D. Pack, "A two-step Hilbert transform method for 2D image reconstruction," supra and Appendix). From here, the argument λ is dropped from vectors $s_0$, $s_0'$ and $n_0$ for more readability. The differentiated projections are backprojected from the virtual source trajectory $s_0$:

$$b_0(x_0) = \int_{\lambda_1}^{\lambda_2}\frac{w(s_0\cdot n_0, n_0)\cdot\text{sgn}(\theta\cdot n_0)\frac{\partial}{\partial\lambda}g_0(\lambda, \alpha_0)}{\|x_0 - s_0\|}d\lambda, \qquad (14)$$

where $$n_0 = s_0' - [\alpha_0\cdot s_0']\cdot\alpha_0, \qquad (15)$$

$$\alpha_0 = (x_0 - s_0)/\|x_0 - s_0\|, \qquad (16)$$

$\lambda_1$, $\lambda_2$ are both ends of the backprojection range, and w for $\lambda_i$, is a normalized redundancy weight defined as $$\sum_{i=0}^\infty w(s_0\cdot n_0, n_0) = 1. \qquad (17)$$

Figure 4:
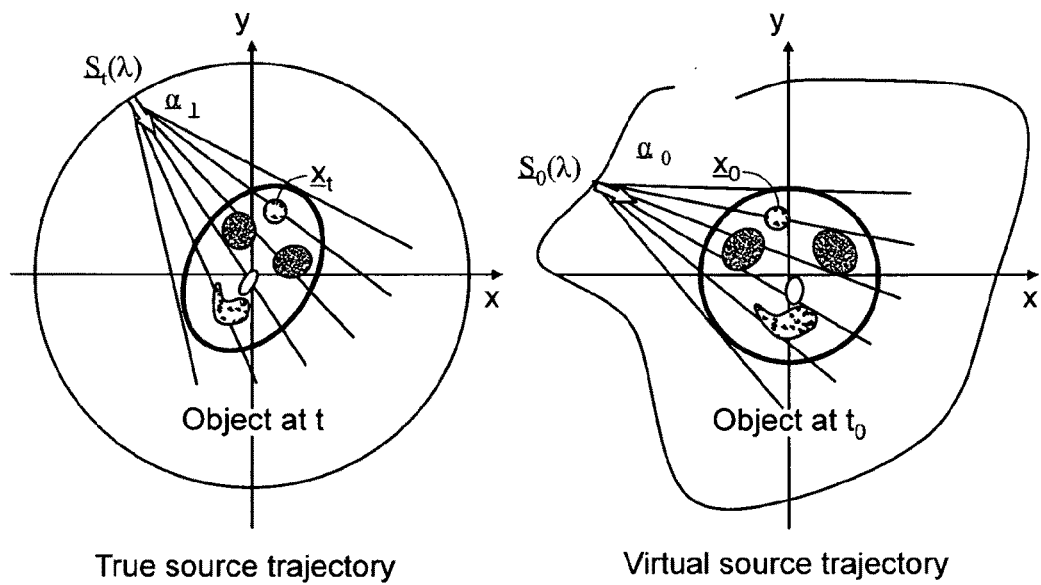
FIG. 4 is an illustrative view of an example of true and virtual source trajectories with rigid motion. Straight lines remained as lines after being transformed from time t to $t_o$.

Finally one obtains $f_0(x_0)$:

$$f_0(x_0) = -\frac{1}{2\pi}H^{-1}(b_0(x_0)), \qquad (18)$$

where $H^{-1}(\bullet)$ is the 1-D finite inverse Hilbert transform along θ direction [see F. Noo, R. Clackdoyle, and J. D. Pack, "A two-step Hilbert transform method for 2D image reconstruction,"]. This method is called DABPF algorithm. Note that globally defined affine transformations preserve straight lines as straight lines (See FIG. 4); thus, DABPF is exact and mathematically the same as Roux's DAFBP.

The DABPF algorithm starts with measured projections and a known time-dependent globally defined affine transform. The DABPF algorithm is summarized by the following four steps that are similar to DBPF algorithm [F. Noo, R. Clackdoyle, and J. D. Pack, "A two-step Hilbert transform method for 2D image reconstruction," supra and Y. Zou and X. Pan, "Exact image reconstruction on PI-lines from minimum data in helical cone-beam CT," *Physics in Medicine and Biology*, vol. 49, pp. 941-959, 2004]. Consider a (u,v) coordinate system (FIG. 5), rotated by angle θ from the (x,y)-axes. Two coordinate systems are related by u(x,y) and v(x,y).

Figure 5:
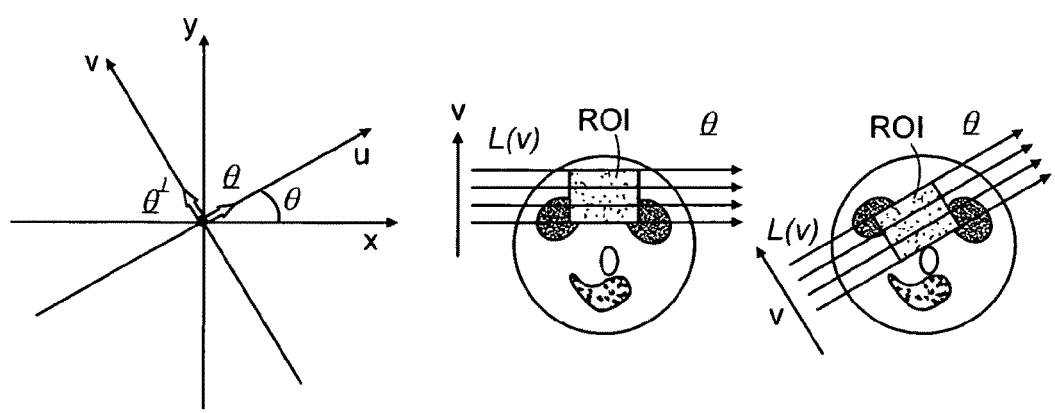
FIG. 5 is an illustrative view of two example of the sets of parallel Hilbert filtering lines. The left case does not need step-4 since $\theta=0$.

[Step 1] Define a region-of-interest (ROI) and a set of the Hilbert lines L(v) such that (a) every point x=(x, y) inside the ROI lies on only one Hilbert line L(v(x,y)) and (b) all line integral projection data passing through any object point on each Hilbert line are measured. In FIG. 5, two examples on how to choose the set of the Hilbert lines are shown.

[Step 2] Along each Hilbert line L(v(x,y)), the derivative backprojection is computed by Eqs. (12)-(14) to obtain the $b_0(u,v)$, 1-D Hilbert transformed image off along θ.

[Step 3] Along each Hilbert line L(v(x,y)), the Hilbert transform is inverted by using the inversion formula of finite Hilbert transform (Eq. (18)) to obtain a function $\hat{f}(u,v)$, which is the same as f(x,y) but is represented on the (u, v) coordinates.

[Step 4] From the relation $f(x,y)=\hat{f}(u(x,y), v(x,y))$, one obtains f(x,y). This step is not necessary if θ=0.

Figure 7:
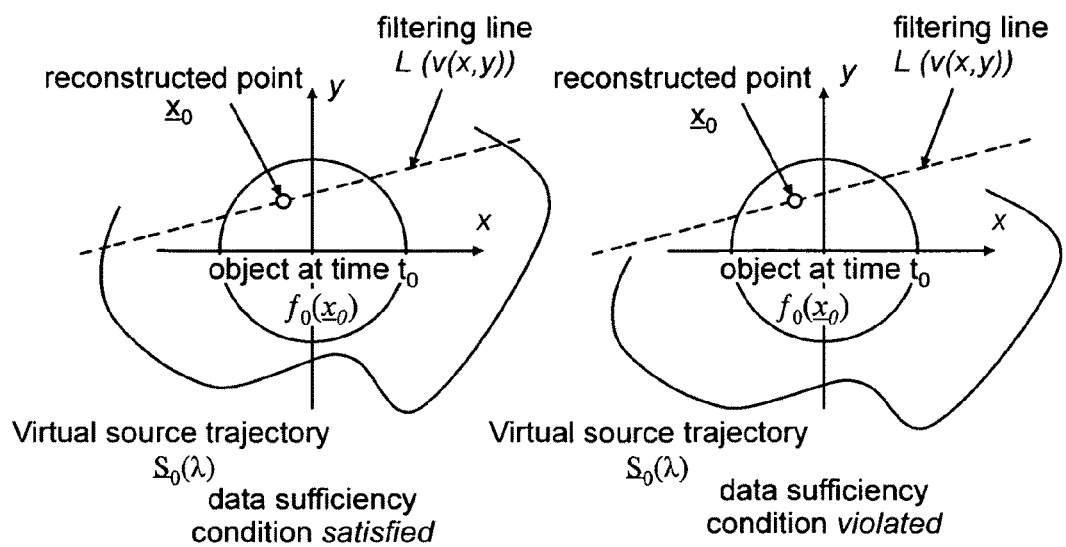
FIG. 7 is an illustrative view showing a point $x_o$ and a virtual source trajectory which satisfy the sufficient conditions described in the Data Sufficiency Condition section for each of the Rigid an Non-rigid Motion Sections (left) and those that do not (right).

Data Sufficiency Condition:

The data sufficiency condition for DABPF is, as a combination of those for DAFBP method [S. Roux, L. Desbat, A. Koenig, and P. Grangeat, "Exact reconstruction in 2D dynamic CT: compensation of time-dependent affine deformations," *Physics in Medicine and Biology*, vol. 49, pp. 2169-2182, 2004; F. Noo, M. Defrise, R. Clackdoyle, and H. Kudo, "Image reconstruction from fan-beam projections on less than a short scan," *Physics in Medicine and Biology*, vol. 47, pp. 2525-2546, 2002] and DBPF method [F. Noo, R. Clackdoyle, and J. D. Pack, "A two-step Hilbert transform method for 2D image reconstruction," supra]: A point $x_0$ at the reference time $t_0$ can be accurately reconstructed from fan-beam projections acquired during a time-dependent affine deformation, provided every line passing through any object point on the filtering line of the point $x_0$ has an intersection with the virtual source trajectory. FIG. 7 provides a graphical description of the condition.

Non-rigid Motion

Figure 6:
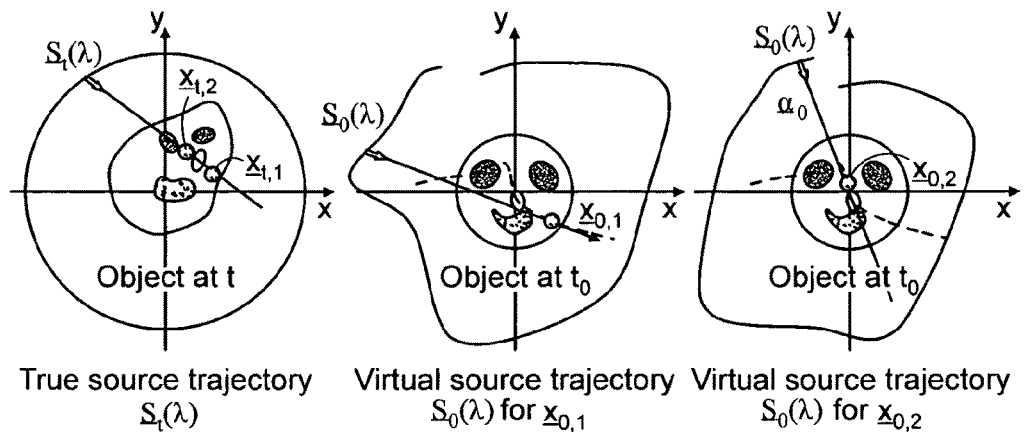
FIG. 6 is an illustrative view of examples of true and virtual source trajectories with non-rigid motion. A straight line at t corresponds to a curve at $t_o$. The proposed DAxBPF applies DABPF on a local basis to approximate the curve by its tangent corresponding to $s_o(\lambda)$ and locally fitted affine transformation for each $x_o$.

In this section, first approximated is a non-rigid motion by a spatially varying affine transformation. Then an approximate algorithm, DAxBPF, is proposed to reduce the effect of the spatially varying time-dependent affine transformation by applying DABPF on a local basis (See FIG. 6).

Spatially Varying Affine Transform:

Considered next are two scenarios how a non-rigid transformation of the object is given: sparsely defined time-dependent affine transformations; or a time-dependent motion vector field.

The first scenario starts with a finite sets of time-dependent affine transformations $\Gamma_{tk}$, $(x_{t,m})$ given only for discrete spatial locations $x_{0,m}$'s, m=1 . . . M, and temporal samples $t_k$'s, k=1 . . . K. Then each element of matrix and vector of affine transform are spatially and temporally interpolated [See Eq. (2)] by, e.g., a cubic spline interpolation, to obtain an affine transformation for each small region-of-interest (ROI) at time t (that corresponds to each projection data). An example is shown in FIG. 8. This scenario is focused on herein.

The second scenario starts with a time dependent motion vector field. The time dependent deformation $M_t(x_t)$, defined by a time-dependent motion vector for each location, projects a point $x_t$ at time t to a point $x_0$ at time $t_0$. The deformation $M_t(x_t)$ has to be bijective (one-to-one and onto) to be invertible. For a small ROI centering $x_t$, a vector field within the ROI can then be approximated by an affine transformation. Applying it for each $x_t$ will generate spatially varying affine transformation.

DAxBPF Algorithm

The DABPF algorithm is applied to compensate for the space- and time-dependent affine transform $\Gamma_{t,m}$ on a local basis. See FIG. 6. Theoretically, each image pixel $x_t$ could have different affine transformation $\Gamma_{t,m}(x_t)$, m=1 ... $N_x^2$, where $N_x$ is the number of pixels along (x, y)-axes. As a pixel-specific compensation is computationally too expensive, the following approach called DAxBPF is proposed.

DAxBPF first reconstructs a finite set of images $f_{0,m}(x_0)$, m=1 ... M ($<<N_x$), at the reference time $t_0$ by using DABPF (Steps 1-4 in Sec. II.B) to compensate for $\Gamma_{t,m}$. And as Step 5, a weighted summation is then applied to images $f_{0,m}(x_0)$ with:

$$f_0(x_t) = \sum_{m=1}^{M} W_{0,m}(x_t) f_{0,m}(x_t) \bigg/ \sum_{m=1}^{M} W_{0,m}(x_t). \quad (19)$$

where $W_{0,m}$ is a spatially varying weight which corresponds to spatially changing elements of affine transformation (FIG. 8). Note that the filtering direction can be independently defined for each ROI.

Data Sufficiency Condition:

Similar to DABPF algorithm, and as Pack, et al., empirically stated in [J. D. Pack and F. Noo, "Dynamic computed tomography with known motion field," in *Medical Imaging 2004: Image Processing*, San Diego, Calif., USA, 2004, pp. 2097-2104], the data sufficiency condition for DAxBPF is as follows: A point $x_0$ at the reference time $t_0$ can be reconstructed from fan-beam projections acquired during a time-dependent non-rigid deformation with better quality, provided every line passing through any object point on the filtering line of the point $x_0$ has an intersection with the virtual source trajectory. The reconstructed point $x_0$ is with better quality than if the condition is not satisfied. Unfortunately, satisfying the condition in itself does not guarantee that the resulting quality of the image is sufficient.

Evaluation Methods

Computer simulations were performed to assess the performance of the proposed algorithms in terms of the following aspects with non-rigid motion: 1) overall motion artifact; 2) spatial resolution; 3) non-periodic motion pattern; 4) the effect of feathering in reconstruction; 5) image noise; 6) tradeoff between image noise and spatial resolution; and 7) off-synchronized motion.

General Methods:

A 5-ball phantom defined in Table 1 was used. Unless otherwise mentioned, the motion of the phantom was as follows: one motion cycle period governed all of balls; the ball #2 in the north rotated over 60° about the origin while the others over 30°; all balls contract to 2:1; all balls translate over (40 mm, 20 mm). Specifically, elements of affine transformation in Eq. (2) are defined as:

$$A_t = C_t \text{Rot}(\phi_t), \quad (20)$$

$$C_t = c_0 + c_1 \cos(2\pi t/T_{RR}), c_0 = 1.5, c_1 = -0.5, \quad (21)$$

$$\phi_t = \phi_0 + \phi_1 \cos(2\pi t/T_{RR}), \quad (22)$$

$$B_{i,t} = B_{i,1} \sin(2\pi t/T_{RR}); i=0,1; B_{0,1}=-20; B_{1,1}=-10, \quad (23)$$

where $\text{Rot}(\phi)$ is a rotation matrix for an angle of $\phi$, $T_{RR}$ is a time period for one motion cycle, $(\phi_0, \phi_1)$ for the north ball and for the others were (30°, −30°) and (15°, −15°), respectively. Three $T_{RR}$'s that correspond to 60, 63 and 67 cycles-per-minute (bpm) were used; their projection ranges were $6\pi/T_{RR}$, $5.71\pi/T_{RR}$, $5.37\pi/T_{RR}$, respectively, with a gantry rotation time of ⅓ s/($2\pi$)≈333.3 ms/rev. At 60 bpm, the object motion cycle and projection rotation cycle are in full-sync: $T_{RR}$ corresponds to $6\pi$. 72 bpm and 90 bpm are next fully-synchronized conditions, $T_{RR}$ to $5\pi$ and $4\pi$, respectively. Taguchi, et al. showed that the effect of object motion simply depends on the extent of such synchronization [K. Taguchi, B. S. Chiang, and I. A. Hein, "Direct cone-beam cardiac reconstruction algorithm with cardiac banding artifact correction," *Medical Physics*, vol. 33, pp. 521-539, 2006]. Thus, studying the motion cycles of 60, 63 and 67 bpm will be sufficient to see the effect of synchronization from a full-sync to a severe off-sync. Among them, the motion with 63 bpm was used intensively.

As the affine elements for the north ball were different from those for the others, the method described above was employed and smoothly changing affine transformations (FIG. 8) were obtained. DABPF used the affine transformation defined for balls #1, #3, #4, and #5.

Fan-beam projection data were generated over $8\pi$ with ⅓ s/($2\pi$)≈333.3 ms/rev and monochromatic x-ray at 80 keV. The other scan conditions were similar to a clinical x-ray CT scanner: Equiangular 672 samples over 52.14°; 1160 projections per $2\pi$; the source-to-isocenter distance of 570 mm. An example of generated projection data is shown in FIG. 8.

Circular images were reconstructed with a matrix of $512^2$ over a diameter of 500 mm range. During the image reconstruction with DABPF and DAxBPF methods, when the range of backprojection for an x was $n_\lambda \pi$, $n_\lambda \in N^*$, a rectangular weight with a height of $1/n_\lambda$ was used for the normalized redundancy weight w. When the backprojection range was a fraction of $\pi$, $(n_\lambda + \beta)\pi$, $0 < \beta < 1$, a trapezoidal weight was used whose height was $1/n_\lambda$, in the middle region and linearly reduced over $\beta\pi$ to zero at both edges. For $H^{-1}(\bullet)$, $\theta$ was fixed at (1,0), horizontally from left to right; and known pixel value $f_0(x_0)=0$ for $\|x_0\|>220$ mm was used to obtain the offset value. A Shepp-Logan filter and a Parker weight was used for FBP method.

The "true images" were obtained as follows: At each time t, projection data over $8\pi$ was obtained without phantom motion; and an image was reconstructed by FBP with a ⅛ weight.

Overall Motion Artifact and Spatial Resolution:

The 5-cylinder phantom with a 63 bpm motion was used. Images at t=0, $T_{RR}/4$, $T_{RR}/2$, and $3T_{RR}/4$, were reconstructed by FBP, DABPF, and DAxBPF, respectively. The profiles of the images at t=0 and $T_{RR}/2$ are obtained to assess the accuracy of pixel values and the spatial resolution.

Backprojection Range and Feathering:

The projection data with 63 bpm was used. In order to evaluate the effect of a non-periodic object motion, three images were reconstructed by DAxBPF from projections over $2\pi$, $4\pi$, and $6\pi$ (corresponding to 0.35, 0.70, and 1.05 cycles). A rectangular redundancy weight was applied in each case.

At the presence of the object motion, a feathering weight is often applied to reduce the effect of inconsistency in projection data. The ability of such feathering weights to reduce the motion artifacts was assessed. A trapezoidal weight was used and reconstructed images from projections over $2.2\pi$, $4.2\pi$, and $6.2\pi$, respectively, and compared images with a rectangular weight.

Image Noise:

The projection (line integral) data with 63 bpm was converted to the transmitted x-ray intensity with the incident flux of 5,000 photons per ray. Poisson noise was then added and the noisy intensity data were then log-converted back to line integrals. Image reconstruction was employed by FBP and DAxBPF with projections over $2.2\pi$, $4.2\pi$, and $6\pi$, respectively.

Noise-Resolution Tradeoff:

The tradeoff between the image noise and spatial resolution at the expanded and contracted phases with and without motion compensation was evaluated.

Three projection data under 3 motion conditions were used: a) the heart was beating; b,c) the heart was stationary either at t=0 (the expanded phase) or at t=T/2 (the contracted phase). One image each at t=0 and T/2 was reconstructed using DAxBPF algorithm. DAxBPF reduces to DBPF without motion correction. An index of the spatial resolution was then obtained as follows. A horizontal profile near the north ball was obtained in each image (FIG. 9, arrows); the inverse of the maximum gradient of the profile was obtained and normalized by that of the stationary expanded object (t=0).

Poisson noise was added to projection data using the same procedure as described herein. For each of the 3 projection sets, 20 realizations of noisy projection data (60 data sets in total) were generated. One noisy image each at the expanded and contracted phases was reconstructed from each of noisy data from motion condition-a; one noisy image each was reconstructed from each of conditions-b and -c. An index of the image noise was then obtained as follows. The standard deviation (s.d.) for each pixel was computed over the 20 noise realizations. These standard deviations were then averaged over the square region of 110 mm×110 mm (see FIG. 9) and normalized by the average standard deviation obtained from the stationary expanded object (condition-b). The s.d. of s.d. values over the entire image also were computed.

A tradeoff curve of spatial resolution and noise with Gaussian filter strength as the parameter along the curve was obtained: To each image was applied a 21×21 Gaussian filter with various strength and measured the above two indices for noise and spatial resolution.

f-Synchronized Motion:

The effect of two kinds of off-synchronizations, inter-off-sync and intra-off-sync, both of which induces an inconsistency between projections at the beginning and the end of backprojection range, were assessed. In the first experiment, the object motion cycle and the scanner's projection angle were off-sync (inter-off-sync). The cycle of the entire object motion was chosen as 60, 63 and 67 bpm corresponding to a scanner's rotation of $6\pi$/cycle (fully synced), $5.71\pi$/cycle, $5.37\pi$/cycle, respectively. Images were reconstructed from projections over $6\pi$ using DAxBPF.

In the second experiment, the north ball and the other balls were off-sync (intra-off-sync). The north ball followed 60 and 67 bpm while the others did 63 bpm. Images were reconstructed by DAxBPF from data over $6\pi$ and $6.2\pi$.

Evaluation Results

Figure 9:
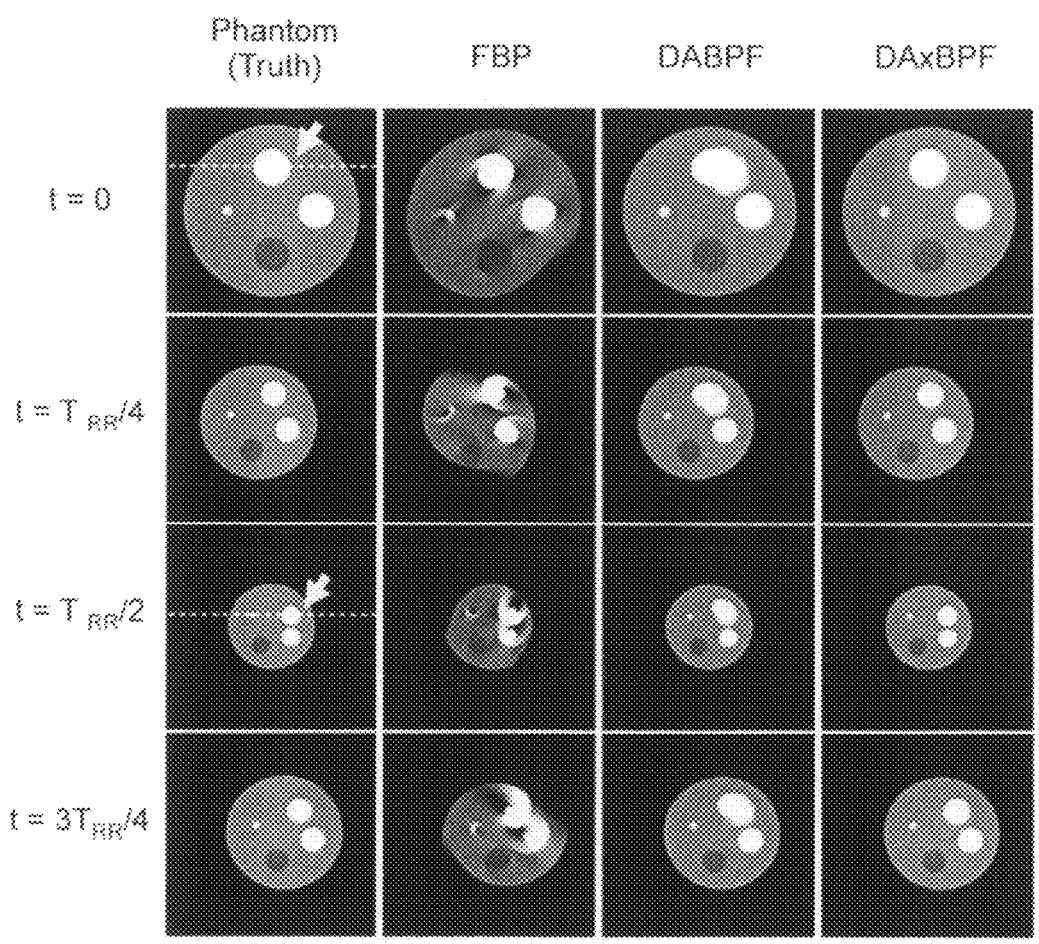
FIG. 9 includes illustrative views of a 5 ball phantom with 63 bpm reconstructed from projections.

Overall Motion Artifact and Spatial Resolution:

FIG. 9 shows images reconstructed by FBP, DABPF, and DAxBPF together with the true phantom images with a narrow window width (0.054 cm$^{-1}$ or 300 H.U.) to enhance the artifact.

Images of FBP exhibited strong shading/whitening artifact and distorted shape of balls. Images of DABPF showed almost no artifact except for severely smeared north ball. The artifact did not spread out to large area as FBP. Images of DAxBPF presented no visible artifacts in all motion phases.

Figure 10:
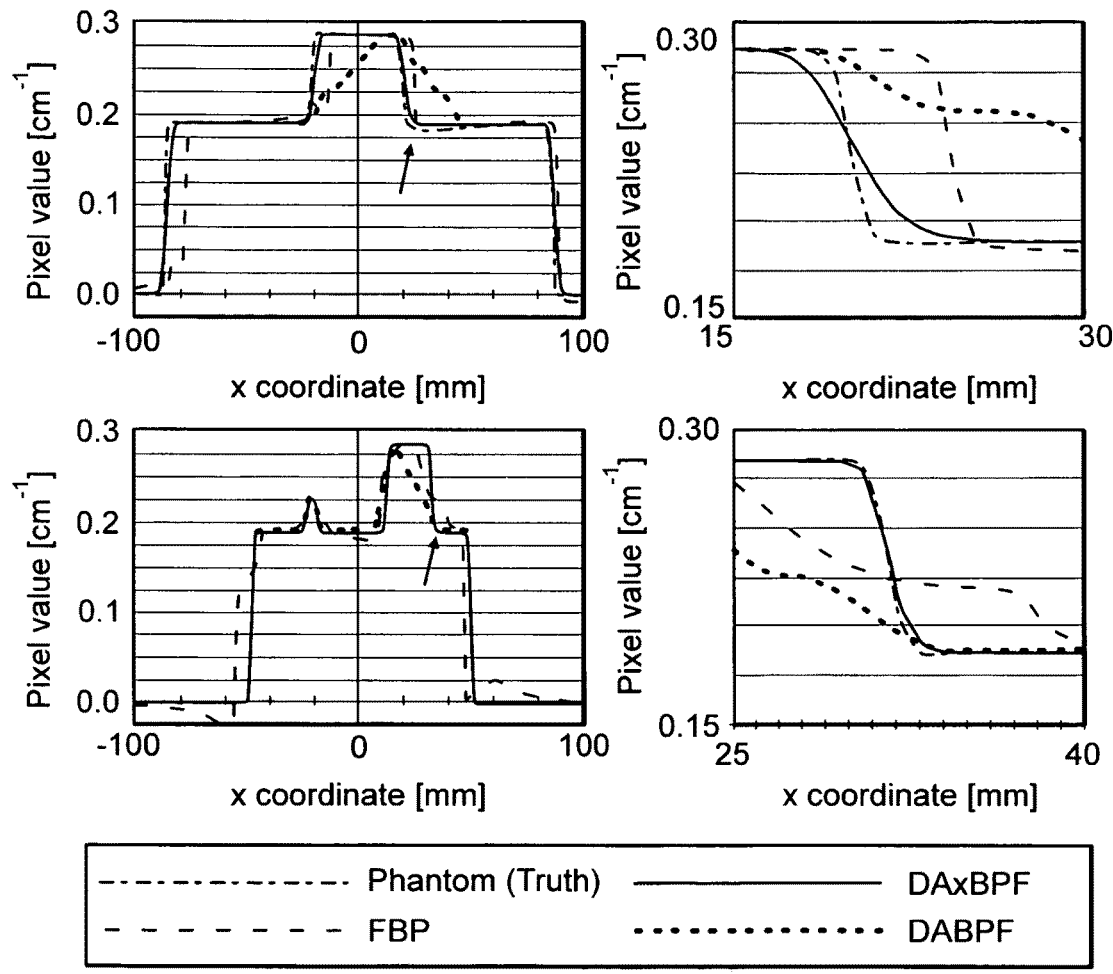
FIG. 10 are graphical views of the horizontal profiles of certain illustrations of FIG. 9.
Figure 15A:
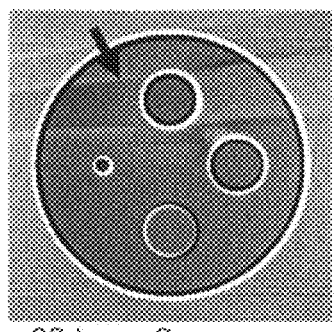
FIGS. 15(a)-(d) are illustrative views of difference images.
Figure 15B:
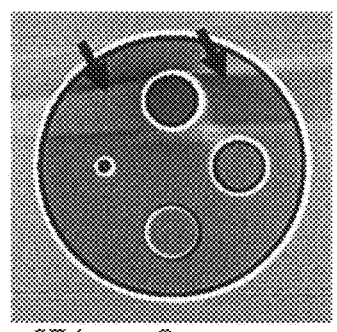
Figure 15C:
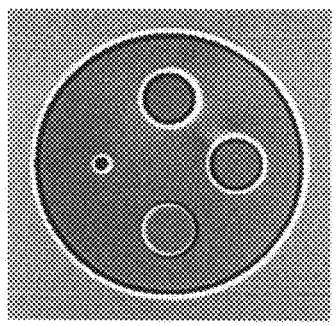
Figure 15D:
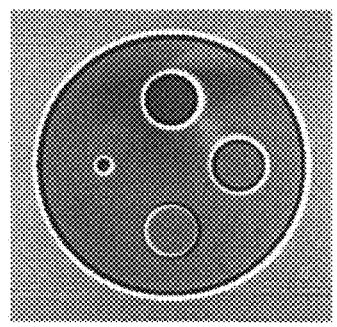
Figure 16:
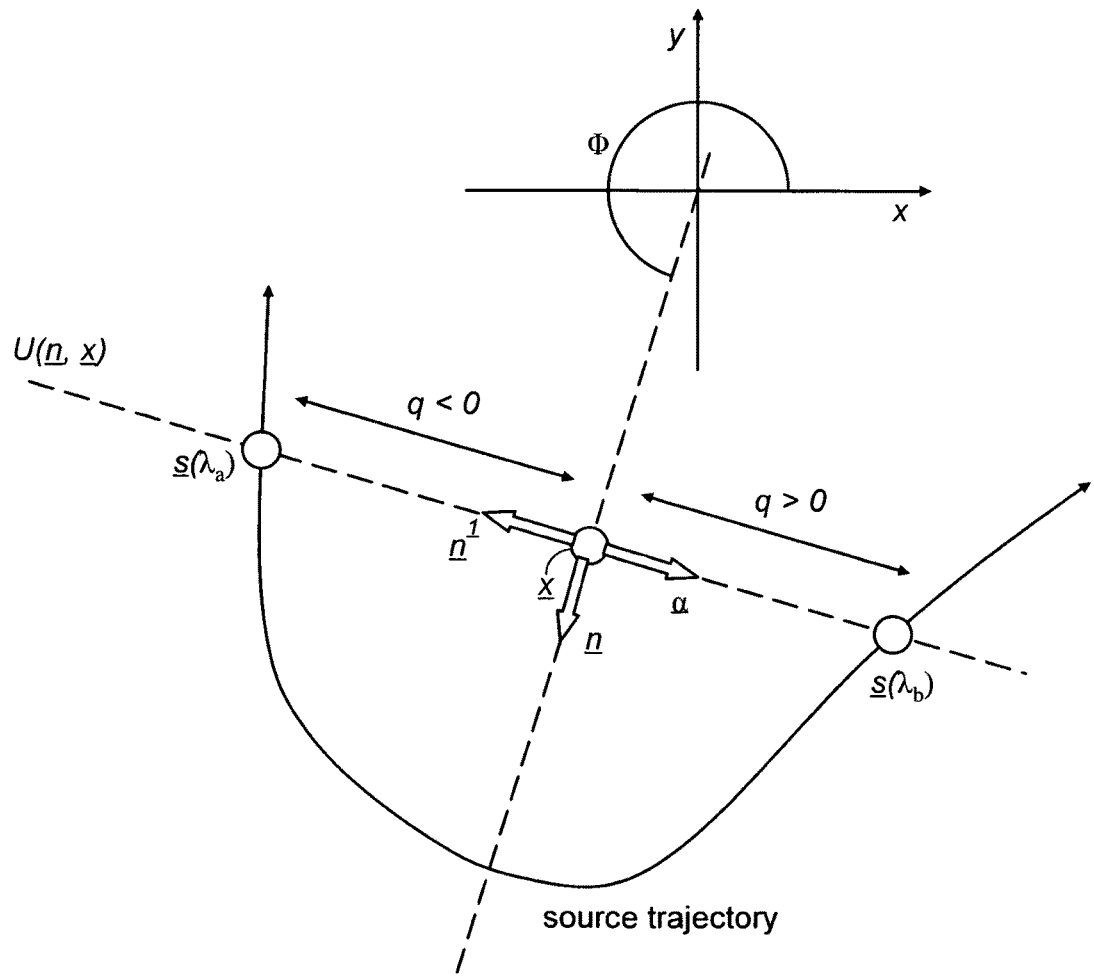
FIG. 16 is an illustrative view illustrating of a line passing through a point and sources.
Figure 17:
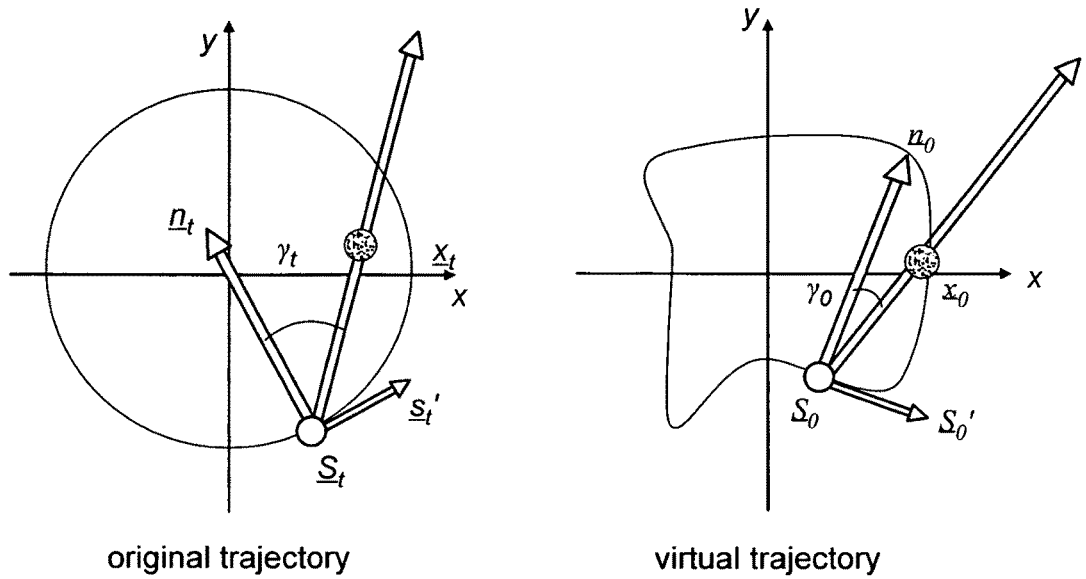
FIG. 17 illustrates scaling and translation move x-ray source $s_t$ and the point of reconstruction $x_t$. Notice the fan-angle in the virtual trajectory is defined by the vectors tangent and normal to the source trajectory.

Horizontal profiles at t=0 and $T_{RR}/2$ shown in FIG. 10 confirmed the above observations: FBP provided shifted or distorted profiles; DABPF also showed distorted profiles; the edge of DAxBPF was slightly blurred at t=0 but values in flat regions were accurate.

Two observations on edge profiles of DAxBPF are made. First, they were more blurred than that of FBP in general; and second, the sharpness of edges was phase dependent. DAxBPF provided sharper edge profiles at t=$T_{RR}/2$ (contracted phase) than those at t=0 (expanded phase)—in fact, the profiles at t=$T_{RR}/2$ are very close to the "truth," FBP without object motion.

It is believed that the common causes of the two phenomena must be the derivative process with respect to $\lambda$ and the motion compensation process. When derivative is calculated by differentiating adjacent samples as in Eq. (13) and if those samples are spatially separated in a larger distance than adjacent rays used in the ramp filtering of FBP, the derivative process reduces the spatial resolution. This is a common problem with other methods that use a differentiating step.

The interval of samples is transformed as $n_0 = A_t n_t$ during the motion compensation process. The intrinsic Nyquist frequency $f_{Ny}$, defined by the sampling intervals along $n_t$ at t is then converted to $f_{Ny}/\|A_t n_t\| > 1$ at the reference time $t_0$. The image at the expanded phase t=0 is reconstructed with $\|A_t n_t\| > 1$ for almost all projections, which results in the reduced Nyquist frequency, so as the spatial resolution of images. In contrast, the image at the contracted phase t=$T_{RR}/2$ is reconstructed with $\|A_t n_t\| < 1$, thus, shows the improved spatial resolution. If the scale of the object is not isotropic (i.e., scales along x- and y-axes are different from each other), it may cause a phase-dependent asymmetric point spread function.

Backprojection Range and Feathering:

FIGS. 11a-11c show images reconstructed by DAxBPF from $2\pi$, $4\pi$, and $6\pi$, respectively. The effect of non-periodic motion patterns during the backprojection range was seen as shadings (arrow) and white cloud (curved arrow) in FIGS. 11a ($2\pi$) and 11b ($4\pi$). Notice, however, a very narrow window width is used to enhance the shading, which is merely 0.002 cm$^{-1}$ or a 3.2% of the difference between the north ball and ball #1 (on center). The relative rotating motion between the north ball and the rest of the phantom over $2\pi$ was 21°, which was twice as large as the rotating motion over $\pi$ (10.5°). Comparing FIG. 11a with the FBP in FIG. 9, it is found that the proposed local correction worked noticeably well to reduce the effect of non-rigid motion.

The visibility of the shading artifact was significantly reduced by using a slight overlap ($0.2\pi$) with a trapezoidal feathering weight (FIGS. 11d-11f)—although the reduced pixel value remained.

Image Noise:

FIGS. 12(a)-12(d) shows reconstructed noisy images at t=0. In order to compare image noise with the same point spread function, a 7×7 Gaussian filter was applied to the image reconstructed by FBP to produce FIG. 12a. A square ROI was used at the iso-center to measure the standard deviation (s.d.) of pixel values, which was normalized against that of filtered FBP image. The normalized s.d. value of DAxBPF method decreased with increasing backprojection range: 0.85 with 2.2π, 0.46 with 4.2π, and 0.40 with 6π, respectively. These results generally agree with a simple theoretical prediction by the amount of effective photons contributed to images: $(\pi/2\pi)^{1/2}=0.71$, $(\pi/4\pi)_{1/2}=0.50$, and $(\pi/6\pi)^{1/2}=0.41$.

Noise-Resolution Tradeoff:

FIG. 13(b) shows s.d. values computed over 20 noise realizations at t=0 with the beating phantom. The s.d. reduced to 1.7:1 with all of four cases with increasing a distance from the center from 0 to 100 mm. There was no angular dependency.

FIG. 13(a) shows four tradeoff curves. Four observations were made: (1) When the object was stationary, images at the two phases had different noise level at the same spatial resolution; (2) when the object was beating, images at the two phases had different spatial resolutions; (3) at the expanded phase, the tradeoff curve for the beating phantom is inferior to that for the stationary phantom; and (4) at the contracted phase, the tradeoff curve for the beating phantom indicates a better performance than for the stationary phantom.

The first observation is attributed to the difference in phantom size. Larger objects attenuate x-ray photons more, and produce noisier projection data (and reconstructed images) for a given incident x-ray photon flux. And the discussion herein explains the mechanism of the second observation.

A further study is required to understand the nature of the tradeoffs, observations 3 and 4, in detail. However, it is believed that the logarithm conversion process may be the major cause. Photon noise in acquired x-ray intensity data is Poisson distributed in this study (it will be compound Poisson with additive electronic noise in actual data), which is log-converted for line integrals and then scaled during the motion compensation process of DAxBPF. This non-linear process may introduce a favorable tradeoff for DAxBPF when images at the contracted phase were reconstructed. Since the gain/loss of tradeoff curves must depend on the shape and the motion of the object, we cannot definitively conclude that this property is or is not an advantage of DAxBPF when applied to clinical patient data.

Off-Synchronized Motion

FIG. 14 shows difference images with and without intersynchronization from the image of FBP with a stationary object at t=0. The motion cycle of the entire object and the rotation cycle of the scanner were in full-sync (a, 60 bpm), moderately off-sync (b, 63 bpm), and largely off-sync (c, 67 bpm). Both images with out-of-sync were almost identical to a fully-synchronized case (60 bpm), demonstrating the robustness of DAxBPF algorithm.

FIG. 15 presents difference images with intra-off-sync from the image of FBP with the stationary object. A negligible level of derivation of pixel values ($\pm 0.0002$ cm$^{-1}$, 1 H.U., ±0.1%) was observed (arrows), which was in fact reduced by applying the feathering.

Discussion and Conclusion

An exact DABPF algorithm is developed that compensates for a time-dependent affine transformation of the object. Also developed is an approximate algorithm, DAxBPF, to reduce the effect of no-rigid motion of the object. The results showed that an approximate DAxBPF algorithm, which applies DABPF on a local basis, reconstructs images with good quality. DAxBPF significantly reduces the motion artifact compared with the current cardiac algorithm (FBP with Parker weight). The proposed DAxBPF also reduces the image noise when it uses projections over a larger range than Parker weight does. A 60% noise reduction from the current level, if directly converted, implicates an 83% dose reduction from the current level (from 10-15 mSv to 1.7-2.6 mSv) to obtain images with the current noise level.

The results show that the reconstruction from projections over 2π is likely to be acceptable; yet images over 6π or quasi-one cycle is better in terms of the intensity of artifacts and image noise. The use of data over one heart cycle is practically possible in clinical settings. The current cardiac CT protocols choose a helical pitch between 0.2-0.33 (corresponding to 6π-10π for each point x) depending on the patient heart rate, such that each point x is covered at least over one heart cycle.

The affine motion model does not preserve the mass of the object as it deforms. It proportionally changes the mass with the scale. This motion model may not be a right one for various motions of human body. However, as the heart expands and contracts, iodine-mixed blood comes into and goes out of chambers (e.g., left ventricle), which drastically increases and decreases the total mass. Thus, in fact, affine transform is a better model for cardiac imaging than those which preserve the mass.

A natural question one may ask is, "Why does DAxBPF work well for non-rigid motion?" Intuitive reasoning is a slow and quasi-periodic object motion relative to the projection angle. Let us consider an object which consists of a finite set of delta functions and assume a non-rigid motion simply moves their locations, $f(x)=\Sigma_m \delta(x_m)$, where m is an index for delta functions. The filtered parallel projection data can then be decomposed into a finite set of sinograms. With non-rigid motion, the backprojection (integration) process introduces an error at a point x as each sinogram is radially shifted due to the motion of the delta function at $x_{m,t}$, for each time t. The effect of such shift introduces inaccurate values, weights and integration range. If the motion within the integration range is drastic, the effect is significant. However, if the motion is slow and smooth within the angular range, the error remains small. A quasi-periodic motion over the angular range also reduces the inconsistency between the beginning and the end of angular range, thus, reduces the artifact. Phantoms with various off-sync and non-periodic motions reasonable in cardiac imaging (FIGS. 9, 11-12) were tested and good results were obtained.

The proposed DAxBPF will provide good images even at the presence of transverse truncation as DBPF does. As DAxBPF does not require projection data outside of the region-of-interest and its filtering lines, it also has a potential to reduce necessary radiation dose to the patient in cardiac scan.

DAxBPF is computational intensive. If M sets of motion models are used along each filtering line, DAxBPF will first reconstruct M images, and then apply a weighted summation. Thus, DAxBPF requires $O(M\ N^3)$ for finite inverse Hilbert transform and $O(M\ N^3)$ for backprojection process. Therefore, DAxBPF algorithm will be approximately M times computationally demanding than the current FBP methods. The appropriate number of motion models in one dimension, M, depends on the complexity of the motion, thus, is of interest in future works. From literatures for modeling and estimation of cardiac motion, it is assumed that 10-30 would be sufficient to cover the human heart (100 mm) with which the non-rigid motion over 3-10 mm range is approximated by one rigid motion model.

The extension of the proposed fan-beam DAxBPF method to cone-beam reconstruction is relatively straightforward. The derivative of cone-beam projections is taken with respect to the source parameter, $\lambda$, followed by a weighted cone-beam backprojection and a 1-D finite inverse Hilbert transform. The optimal filtering direction of 1-D Hilbert transform is an interest of the research. Candidates include an actual PI-line formed by virtual trajectory and a virtual PI-line that does not connect two source points in either virtual or actual trajectories.

In conclusion, there are developed fan-beam reconstruction algorithms using derivative backprojection filtering approach to compensate for a time-dependent deformation. DABPF method for a global affine transformation is exact. DAxBPF for a non-rigid transformation are approximate, which showed promising results with computer simulations.

FBP$_x$ Algorithm

Herein, presented is a slightly modified Schafer's method (FBPx) that is exact if the motion of the object can be described by a class of time-dependent affine transformation-sotropic scaling (contraction and expansion), rotation, and translation. Schafer et al. have proposed an empirical algorithm, which merely "trace" the motion of each voxel during the backprojection process [Schafer, D., et al., *Motion-compensated and gated cone beam filtered backprojection for 3-D rotational X-ray angiography*. Medical Imaging, IEEE Transactions on, 2006. 25(7): p. 898-906; van Stevendaal, U., et al. Motion-compensated reconstruction in helical cardiac CT. in the 9th international conference on fully three-dimensional reconstruction in radiology and nuclear medicine. 2007. Lindau, Germany].

Theories

Geometry and Deformation:

The right hand coordinate system is used and the time-dependent two-dimensional deforming object is defined by $f_0(x_0)$, $x_0 \in R^2$, at the reference time $t=t_0$, and $f_t(x_t)$, $x_t \in R^2$, at time t. The time-dependent affine operation $\Gamma_t$ projects a point $x_t$ at time t to a point $x_0$ at time $t_0$:

$$\Gamma_t(x_t)=A_t x_t+b_t=x_0, \quad (1.1)$$

where the affine matrix $A_t$ consists of a isotropic scaling $c_t$ and a rotation by $\theta_t$ and $b_t$ is a translation vector $$A_t=c_t \text{Rot}(\theta_t) \text{ and } b_t=(b_1(t), b_2(t))^T. \quad (1.2)$$

Note that neither shear nor direction-dependent scaling is allowed; the deformation defined here is a subset of affine transformations.

The object can then be noted by $$f_t(x_t)=f_0(\Gamma_t(x_t))=f_0(x_0). \quad (1.3)$$

The circular source trajectory and fan-beam projections can be expressed as:

$$s_t(\lambda)=(-R \sin \lambda, R \cos \lambda)^T, \quad (1.4)$$

$$g_t(\lambda,\alpha_t)=\int_0^\infty f_t(s_t(\lambda)+l\alpha_t)dl \quad (1.5)$$

where $\alpha_t=(-\sin \alpha, \cos \alpha)^T$ is a unit vector along a ray and R is the distance from the source to the rotation axis. Note that source parameter is monotonically increasing function of time, for example, $\lambda=at$.

Motion Compensation in Projection Domain:

Projection data at time t, $g_t$, can be related to those at the reference time $t_0$, $g_0$ by $$g_0(\lambda,\gamma_0)=c_t \times g_t(\lambda,\gamma_t); \ g_0(\lambda,\alpha_0)=c_t \times g_t(\lambda,\alpha_t), \quad (2.1)$$

where $\alpha_0=A_t\alpha_t/\|A_t\alpha_t\|$ and local angular parameters $\gamma_0$ and $\gamma_t$ correspond to $\alpha_0$ and $\alpha_t$, respectively.

Proof:

Using Eq. (1.3), the object f at time t is described by $f_t(s_t(\lambda)+l\alpha_t)=f_0(s_0(\lambda)+lA_t\alpha_t)$. Inserting it into Eq. (1.5), one gets $$g_t(\lambda, \alpha_t) = \int_0^\infty f_0(s_0(\lambda)+lA_t\alpha_t)dl = \quad (2.2) \ [Q.E.D.]$$

$$\frac{1}{\|A_t\alpha_t\|}\int_0^\infty f_0\left(s_0(\lambda)+\hat{l}\frac{A_t\alpha_t}{\|A_t\alpha_t\|}\right)d\hat{l} =$$

$$\frac{1}{\|A_t\alpha_t\|} \times g_0(\lambda, \alpha_0) = \frac{1}{c_t} \times g_0(\lambda, \alpha_0).$$

Figure 18:
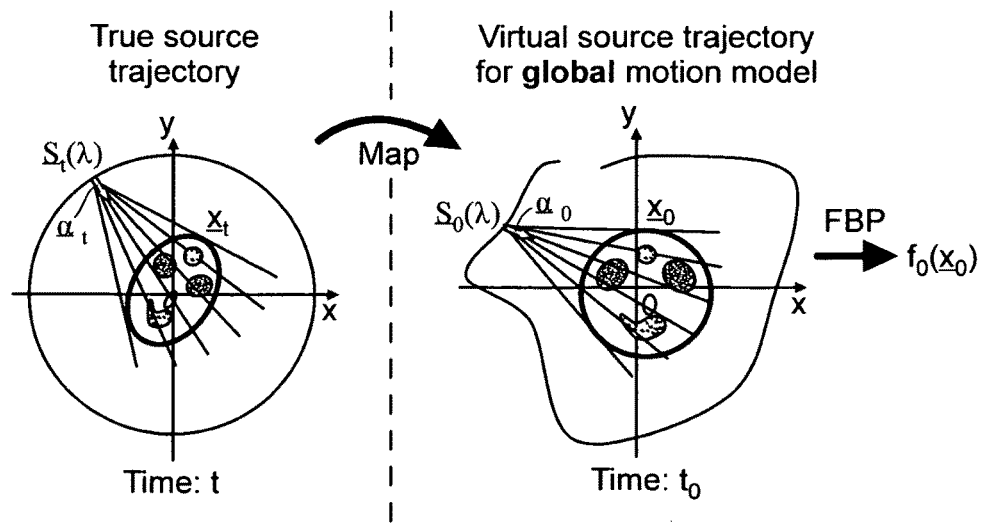
FIG. 18 illustrates a conceptual explanation of motion compensation process.

Note that this transform a circular source orbit $s_t(\lambda)$ around the object $f_t$ into a virtual (usually non-circular) source trajectory $s_0(\lambda)$ around the object $f_0$ at $t_0$: $s_0(\lambda)=\Gamma_t(s_t(\lambda))$. Note also that in the virtual source trajectory, the ray angular parameter $\gamma_0=0$ for the ray which is normal to the source trajectory (see FIG. 18).

One can reconstruct the object at the reference time $t_0$, $f_0$, from projections $g_0$ along the virtual path $s_0$ by using a generalized fan-beam reconstruction formula. Let us call this AFBP algorithm $$f_0(x_0) = \quad (2.3)$$

$$\frac{1}{2}\int_{\Lambda_0} \frac{\|s_0'(\lambda)\|}{\|x_0-s_0(\lambda)\|^2} \int_{-\infty}^\infty w(\lambda, \gamma_0)\cos\gamma_0' g_0(\lambda, \gamma_0')h_R(\gamma_0-\gamma_0')d\gamma_0'd\lambda.$$

where the ramp filtering $h_R(u)$ is defined by $(u/\sin u) h_R'(u)$ and $h_R'(u)=\int|\omega|\exp(j2\pi u\omega)d\omega$, and w is a weight to compensate for the redundancy of samples.

Motion Tracking Schafer's and FBPx Algorithms:

Schafer, et al. proposed a simple motion compensated backprojection algorithm for C-arm cone-beam computed tomography imaging of the coronary arteries. The algorithm consists of the following three parts: (1) multiply the projection data g by a cosine of each ray angle; (2) convolve the preweighted projections with a ramp filter $h_R$; and (3) choose and backproject the filtered data with an inverse square distance weight taking into account the motion of a point of reconstruction ($x_0 \rightarrow x_t$ and $\gamma_0 \rightarrow \gamma_t$). No redundancy weight such as Parker's is used in Schafer's formula; and the backprojection range $\Lambda$, is determined by acquisition geometry at time t, for example, $\Lambda_t=\lambda=[0, 2\pi)$. As von Stevendaal, et al. did, by adding a redundancy weight w defined at time t, Schafer's algorithm can be generally described by the following formula.

$$f_0(x_0) = \quad (3.1)$$

$$\frac{1}{2}\int_{\Lambda_t} \frac{\|s_t'(\lambda)\|}{\|x_t-s_t(\lambda)\|^2} \int_{-\infty}^\infty w(\lambda, \gamma_t)\cos\gamma_t' g_t(\lambda, \gamma_t')h_R(\gamma_t-\gamma_t')d\gamma_t'd\lambda.$$

Note that all of variables are defined at time t in Eq. (3.1) as opposed to at reference time $t_0$ in Eq. (2.3). The redundancy weight w, a view weighting and backprojection range $\Lambda_0$ to those defined at the reference time $t_0$, is changed and there is obtained a slightly modified motion compensated backprojection (FBPx) algorithm.

$$f_0(\underline{x}_0) = \frac{1}{2}\int_{\Lambda_t} \frac{\|\underline{s}'_t(\lambda) + A_t^{-1}(A'_t\underline{s}_t(\lambda) + \underline{b}'_t)\|}{\|\underline{x}_t - \underline{s}_t(\lambda)\|^2} \quad (3.2)$$
$$\int_{-\infty}^{\infty} w(\lambda, \gamma'_t)|e_1\cos\gamma'_t + e_2\cos\gamma'_t|g_t(\lambda, \gamma'_t)h_R(\gamma_t - \gamma'_t)d\gamma'_t d\lambda,$$

$$e_1 = \frac{\underline{s}'_t(\lambda) + A_t^{-1}(A'_t\underline{s}_t(\lambda) + \underline{b}'_t)}{\|\underline{s}'_t(\lambda) + A_t^{-1}(A'_t\underline{s}_t(\lambda) + \underline{b}'_t)\|}\setminus(-\cos\lambda, -\sin\lambda)^T, \quad (3.3)$$

$$e_2 = \frac{\underline{s}'_t(\lambda) + A_t^{-1}(A'_t\underline{s}_t(\lambda) + \underline{b}'_t)}{\|\underline{s}'_t(\lambda) + A_t^{-1}(A'_t\underline{s}_t(\lambda) + \underline{b}'_t)\|}\setminus(-\sin\lambda, \cos\lambda)^T. \quad (3.4)$$

The difference from Schafer's algorithm is only the numerator of backprojection weight and cosine weight applied prior to the convolution process. Note also that the backprojection range $\Lambda_t$ should satisfy data sufficiency condition at the acquisition time t with $\underline{s}_t(\lambda)$ for each reconstruction point $\underline{x}_t$ or at the reference time $t_0$ with $\underline{s}_0(\lambda)$ for each reconstruction point $\underline{x}_0$.

Let us show FBPx algorithm is equivalent to AFBP method, Eq. (2.5). By using Eq. (1.1), the denominator of Eq. (3.2) can be modified as $$\frac{1}{\|\underline{x}_t - \underline{s}_t(\lambda)\|^2} = \quad (3.5)$$
$$\frac{c_t^2}{\|A_t(\underline{x}_t - \underline{s}_t(\lambda))\|^2} = \frac{c_t^2}{\|A_t\underline{x}_t + \underline{b}_t - (A_t\underline{s}_t(\lambda) + \underline{b}_t)\|^2} = \frac{c_t^2}{\|\underline{x}_0 - \underline{s}_0(\lambda)\|^2}.$$

The numerator of the backprojection weight in Eq. (3.2) can be modified as $$\|\underline{s}'_t(\lambda) + A_t^{-1}(A'_t\underline{s}_t(\lambda) + \underline{b}'_t)\| = \|A_t^{-1}(A_t\underline{s}'_t(\lambda) + A'_t\underline{s}_t(\lambda) + \underline{b}'_t)\| \quad (3.6)$$
$$= \|A_t^{-1}(\underline{s}'_0(\lambda))\|$$
$$(\because \underline{s}_0(\lambda) = A_t\underline{s}_t(\lambda) + \underline{b}_t)$$
$$= \|\underline{s}'_0(\lambda)\|/c_t(\because \text{Eq. (1.2)}).$$

One also has in Eq. (2.1)
$$g_t(\lambda, \gamma_t) = g_0(\lambda, \gamma_0)/c_t, \quad (2.1)$$

shown again
and using Eq. (3.6), there is now shown $$e_1 = \frac{A_t^{-1}\underline{s}'_0(\lambda)}{\|A_t^{-1}\underline{s}'_0(\lambda)\|} \setminus \frac{\underline{s}'_t(\lambda)}{\|\underline{s}'_t(\lambda)\|} = \cos\delta \text{ and} \quad (3.7)\text{-}(3.8)$$

$$e_2 = \frac{A_t^{-1}\underline{s}'_0(\lambda)}{\|A_t^{-1}\underline{s}'_0(\lambda)\|} \setminus \frac{\underline{s}_t(\lambda)}{\|\underline{s}_t(\lambda)\|} = \sin\delta,$$

and $$|e_1\cos\gamma'_t + e_2\cos\gamma'_t| = \cos(\gamma'_t - \delta). \quad (3.9)$$

Figures 19, 20:
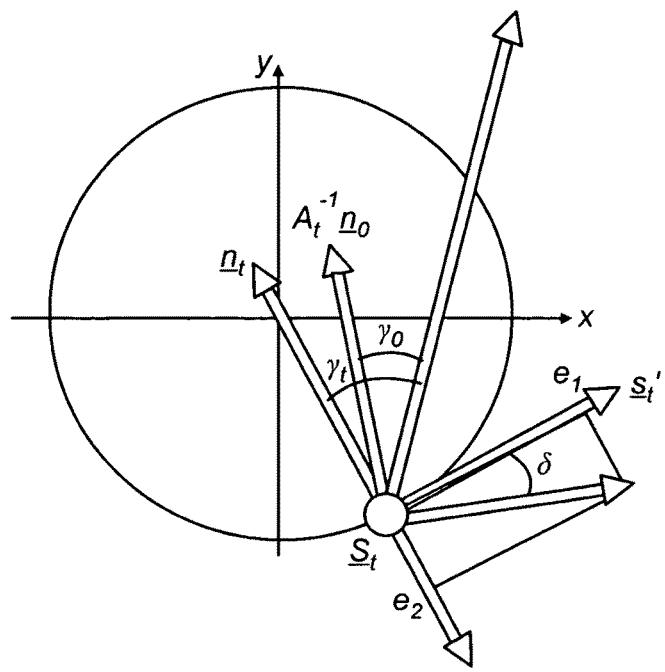
FIG. 19 illustrates a normal vector $n_0$ at the reference time is projected onto the acquisition time t, which is shifted by $\delta$ from the normal vector at t, $n_t$.
FIG. 20 is a tabulation defining a 5-ball phantom. Numbers are in mm for the centers and sizes and in $cm^{-1}$ for linear attenuation coefficients $\mu$.

See FIG. 19 for graphical explanations. Note that $\gamma_t$-$\delta\gamma_0$.

Inserting Eqs. (3.3)-(3.9), and (2.1) into Eq. (3.2) yields AFBP formula, Eq. (2.3).

Therefore, FBPx is exact when the motion of the object can be limited to isotropic scaling, rotation, and translation. Surprisingly, the isotropic scaling parameters $c_t$'s in Eqs. (3.5), (3.6), and (2.1) cancel out while Eq. (3.9) provides correct definition of ray-angle at the reference time, $\gamma_0$.

Similar to Eq. (3.6), one has $$\|\underline{s}'_t(\lambda)\| = \|A_t^{-1}(\underline{s}'_0(\lambda) - (A'_t\underline{s}_t(\lambda) + \underline{b}'_t))\| \quad (3.10)$$
$$= \|\underline{s}'_0(\lambda) - (A'_t\underline{s}_t(\lambda) + \underline{b}'_t)\|/c_t.$$

Apply similar changes of variables to Schafer's method yields $$f_0(\underline{x}_0) = \frac{1}{2}\int_{\Lambda_0} \frac{\|\underline{s}'_0(\lambda) - (A'_t\underline{s}_t(\lambda) + \underline{b}'_t)\|}{\|\underline{x}_0 - \underline{s}_0(\lambda)\|^2} \quad (3.11)$$
$$\int_{-\infty}^{\infty} w(\lambda, \gamma_0)\cos(\gamma'_0 + \delta)g_0(\lambda, \gamma'_0)h_R(\gamma_0 - \gamma'_0)d\gamma'_0 d\lambda.$$

Interestingly, the scaling coefficients $c_t$'s are cancelled out in Schafer's method as well. The difference between Schafer's method, Eq. (3.11), and AFBP and FBPx, Eq. (2.3), are the numerator of the backprojection weight and the cosine weight applied prior to the convolution. Schafer's algorithm is not exact in any form of deformation; however, Schafer's method is shown to be a good approximation when the motion is relatively slow compared to the motion of the gantry of the scanner, because both the derivatives in the numerator and $\delta$ in cosine term are small.

Evaluations

Simulation Settings:

A computer phantom was used that consists of a large cylinder of liquid water containing smaller eight cylinders made of the following materials: 0.8% iodine-mixed blood, muscle, dry spine, adipose, blood, diluted Polymethyl Methacrylate (PMMA) (mass density was 1.04 instead of 1.19), dry rib, and ice (solid water).

The performances of Schafer's and FBPx algorithms are evaluated using a computer simulation. A a 5-ball phantom defined in the tabulation provided in FIG. 20 was used. The motion of the phantom was either of the following four conditions: (1) a rotation over ±15°, (2) a scaling of 2:1, (3) a translation of (±80 mm, ±40 mm), and (4) a combination of all of conditions 1-3.

Specifically, elements of affine transformation in Eq. (2) are defined as:

$$A_t = C_t Rot(\phi_t), \quad (4.1)$$

$$C_t = c_0 + c_1 \cos(2\pi t/T_{RR}), c_0 = 1.5, c_1 = -0.5, \quad (4.2)$$

$$\phi_t = \phi_0 + \phi_1 \cos(2\pi t/T_{motion}), \phi_0 = 15°, \phi_1 = -15°, \quad (4.3)$$

$$B_{i,t} = B_{i,1} \sin(2\pi t/T_{motion}); i=0,1; B_{0,1} = -80; B_{1,1} = -40, \quad (4.4)$$

where $Rot(\phi)$ is a rotation matrix for an angle of $\phi$, $T_{motion}$ $nT_{rev}$ is a time period for one motion cycle, respectively. For each motion condition, two motion cycles, $T_{motion}$, were used to change the relative speed of the object motion to the speed of gantry rotation, $T_{rev}$: $T_{motion} = T_{rev}$ for a fast motion and $3 \times T_{rev}$ for a slow motion.

Fan-beam projection data were generated over $8\pi$ with $\frac{1}{3}$ s/($2\pi$)≈333.3 ms/rev and monochromatic x-ray at 80 keV. The other scan conditions were similar to a clinical x-ray CT scanner: Equiangular 672 samples over 52.14°; 1160 projections per $2\pi$; the source-to-isocenter distance of 570 mm.

Circular images were reconstructed by the following three algorithms: FBP with halfscan weight using projections over 180° plus the full fan-angle; Schafer's method over 3 rotations with a uniform weight; and FBPx method over 3 rotations with a uniform weight. Shepp-Logan filter was used for a reconstruction kernel.

Figure 21A:
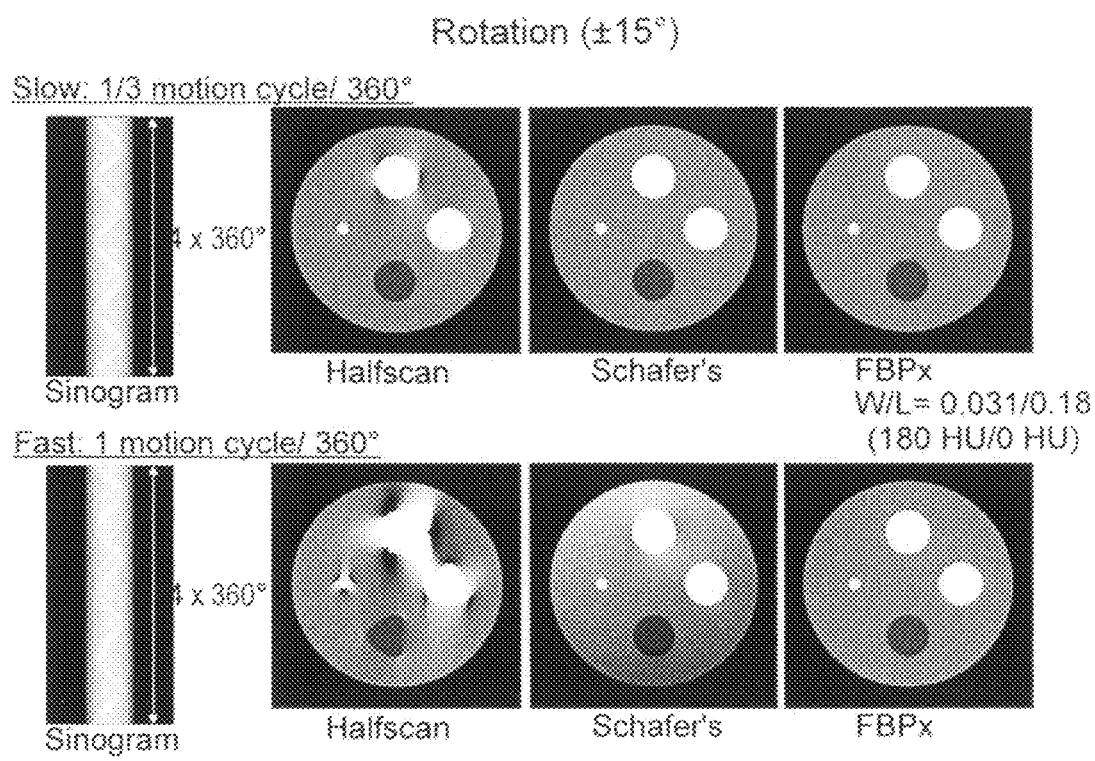
FIGS. 21(a)-(d) include projection data (sinograms) and reconstructed images with four conditions.

Results:

FIG. 21(a) shows projection data (sinograms) and reconstructed images when a rotation is involved. Images reconstructed by halfscan FBP showed strong motion artifacts and distorted object shapes. In contrast, when the rotation of the object is slower, Schafer's algorithm provided nearly an identical image to the image of FBPx. The image of Schafer's exhibited a low frequency shading artifact with faster object motion. The images of FBPx were free from such shading artifacts.

Figure 21B:
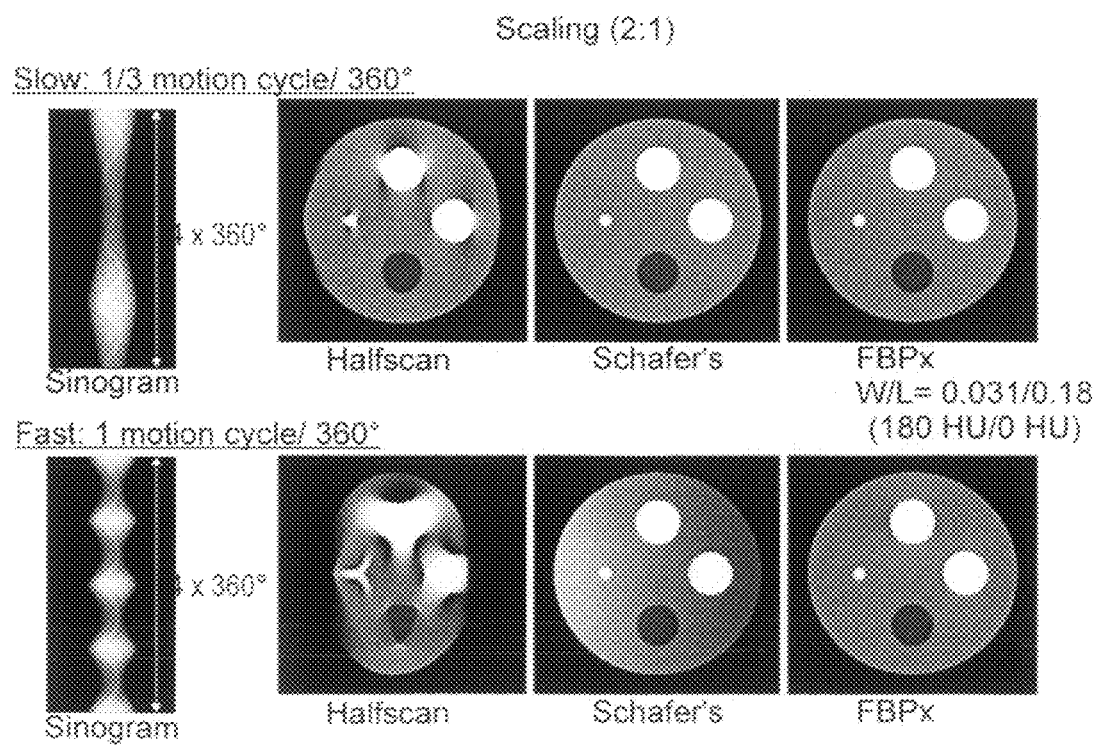

FIG. 21(b) presents results with a scaling. Images reconstructed by halfscan FBP showed strong motion artifacts and distorted object shapes. In contrast, the image reconstructed by Schafer's algorithm was as good as FBPx when the object motion is slower. The image by Schafer's exhibited a low frequency shading artifact with faster motion which was not present with the image of FBPx (bottom row).

Figure 21C:
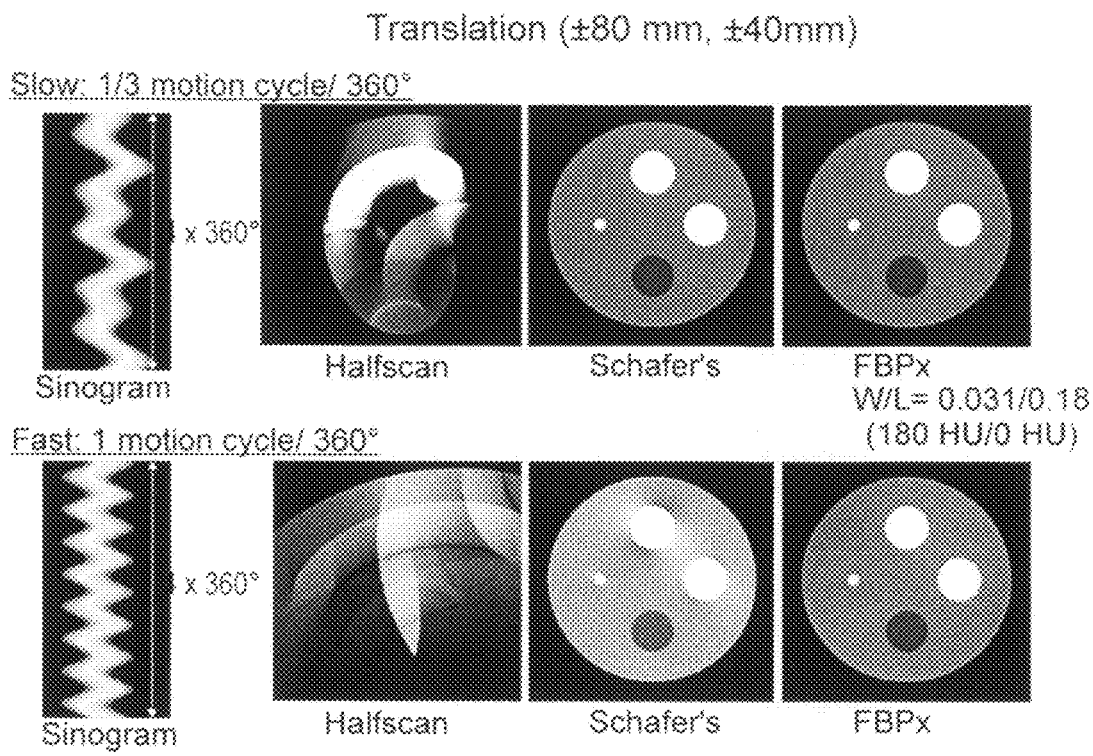

FIG. 21(c) shows results with a translation. Images of halfscan FBP were smeared due to the severe motion. With the slower translation, both Schafer's algorithm and FBPx provided images free from motion artifacts. With the faster translation, Schafer's method exhibited shading artifact as well as a drifted pixel value (DC shift). The image by FBPx showed no artifact.

Figure 21D:
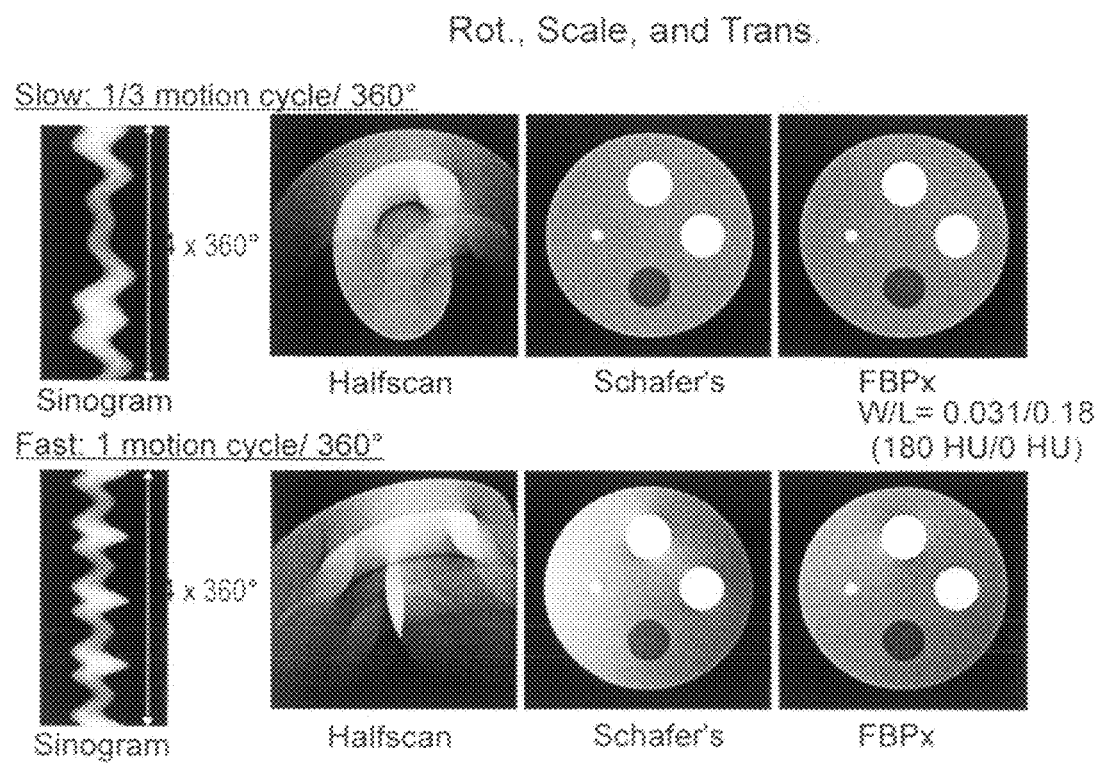

FIG. 21(d) shows results when the motion of the object involves all of the above three components: rotation, scaling, and translation. Halfscan FBP provided images with severe motion artifacts; Schafer's algorithm nearly perfectly compensated for the motion if the object motion cycle is slower while it presented some shading artifacts with faster motion; FBPx provided an exact image with slower motion. The cause of some artifacts seen in the image of FBPx with faster object motion is currently under investigation. It is possible there remains a bug in the program.

Discussion and Conclusions

Schafer's method was modified and it yielded FBPx algorithm. FBPx is exact when the deformation of the object can be described by a combination of a rotation, an isotropic scaling, and a translation. There is shown that the fan-beam and cone-beam versions of Schafer's method are a very good approximation of the exact method. The numerical computer simulations have shown results consistent to these mathematical discussions.

The magic of Schafer's method is that the scaling of projection data cancels out the scaling of the distance between the x-ray source and the point of reconstruction. Thus, the remaining error introduces very limited artifacts. This study can be extended to the parallel-beam version of Schafer's method. One can then imagine that the parallel-beam version of Schafer's algorithm will be (1) exact with translation and (2) less accurate with scaling than the cone-beam counterpart unless the scaling coefficient $c_t$ is added. This is because there is no weight in parallel-beam formulae such as $1/\|x-s\|$ which could cancel out the scaling of projection data.

The parallel-beam version of FBPx algorithm is:

$$f_0(\underline{x}_0) = \qquad (5.1)$$

$$\frac{1}{2}\int_{\Lambda_t}\int_{-\infty}^{\infty}\left\|(A_t'\underline{\lambda}+A_t\underline{\lambda}')\sqrt{\det A_t}-\left(\frac{d}{d\lambda}\sqrt{\det A_t}\right)A_t\underline{\lambda}\right\|w(\lambda)p_t(\lambda,r)$$

$$h_R(r'-r)drd\lambda,$$

where $$\underline{\lambda} = (\cos\lambda,\sin\lambda)^T, \underline{\lambda}' = (-\sin\lambda,\cos\lambda)^T, \sqrt{\det A_t} = c_t. \qquad (5.2)$$

Notice the determinant is added to cancel the effect of scaling in projection data $p_t$.

For the sake Appendix of completeness, there is re-derived with consistent notations fan-beam DBPF algorithm for an arbitrary orbit.

In the reference time or for the stationary object, parallel-beam projection can be expressed as:

$$p(r,\phi)=\int_{-\infty}^{\infty}f(r\underline{n}+r'\underline{n}^\perp)dr', \qquad (24)$$

where $\underline{n}=(\cos\phi,\sin\phi)$, and $\underline{n}^\perp=(-\sin\phi,\cos\phi)$ (see FIG. 13).

DBPF algorithm for a parallel beam projections [23] can be written as:

$$p'(r,\phi) = \lim_{\varepsilon\to 0}\frac{p(r+\varepsilon,\phi)-p(r,\phi)}{\varepsilon}, \qquad (25)$$

$$b(\underline{x}) = \int_{\phi_1}^{\phi_2}w(r,\phi)\text{sgn}(\underline{\theta}\cdot\underline{n})p'(r,\phi)d\phi, \qquad (26)$$

$$f(\underline{x}) = -\frac{1}{2\pi}H^{-1}(b(\underline{x})), \qquad (27)$$

where $H^{-1}(\bullet)$ is the 1-D finite inverse Hilbert transform along $\theta$ direction and w is a normalized redundancy weight that satisfies $$\sum_{i=0}^{\infty}[w(r,\phi\pm 2i\pi)+w(-r,\phi\pm(2i+1)\pi)]=1. \qquad (28)$$

Parallel- and fan-beam projections are related by $$p(r,\phi)=g(\lambda,\alpha)|_{s(\lambda)\cdot\underline{n}=r,\,\alpha\cdot\underline{n}=0}. \qquad (29)$$

Taking a derivative with respect to $\lambda$ of both sides of Eq. (29) yields $$p'(r,\phi) = \frac{g'(\lambda,\underline{\alpha})}{\underline{s}'(\lambda)\cdot\underline{n}}\bigg|_{s(\lambda)\cdot\underline{n}=r,\alpha\cdot\underline{n}=0}. \qquad (30)$$

For simplicity, a prime sign is used to indicate the derivative with respect to $\lambda$ (e.g., $g'\equiv\partial g/\partial\lambda$). This rebinning formula Eq. (30) can only hold for non-zero $s'(\lambda)\cdot n$, thus, the tangent vector $s'(\lambda)$ must not be orthogonal to n. Any source points $s(\lambda_a)$ and $s(\lambda_b)$ on the line U can be parameterized by a distance q:

$$x+q\underline{n}^\perp=\underline{s}(\lambda), \qquad (31)$$

where $|q|=\|x-s(\lambda)\|$. Differentiating each side of Eq. (31) with respect to $\lambda$ yields $$\frac{dq}{d\lambda}\underline{n}^\perp+q\underline{n}\frac{d\phi}{d\lambda}=\underline{s}'(\lambda). \qquad (32)$$

Thus, $$\underline{s}'(\lambda)\cdot\underline{n}=q\frac{d\phi}{d\lambda} \text{ and } \frac{d\phi}{d\lambda}=\frac{\underline{s}'(\lambda)\cdot\underline{n}}{\|x-s(\lambda)\|}. \qquad (33)$$

Inserting Eq. (30) into Eq. (25) and Eq. (33) into Eq. (26) yields a fan-beam BPF formulae for an arbitrary source orbit:

$$g'(\lambda,\underline{\alpha}) = \lim_{\varepsilon\to 0}\frac{g(\lambda+\varepsilon,\underline{\alpha})-g(\lambda,\underline{\alpha})}{\varepsilon}, \qquad (34)$$

-continued $$b_{\underline{\theta}}(x) = \int_{\lambda_1}^{\lambda_2} \frac{w(\underline{s} \cdot \underline{n}, \underline{n}) \text{sgn}(\underline{\theta} \cdot \underline{n}) g'(\lambda, \underline{\alpha})}{\|x - \underline{s}\|} d\lambda. \quad (35)$$

where $$\underline{n} = \underline{s}' - [\underline{\alpha} \cdot \underline{s}'] \cdot \underline{\alpha}, \quad (36)$$

$$\underline{\alpha} = (x - \underline{s})/\|x - \underline{s}\|. \quad (37)$$

and the sum of the redundancy weights to rays from $\lambda_i$ that belong to the same line passing through a point x is 1:

$$\sum_{i=0}^{\infty} w(\underline{s} \cdot \underline{n}, \underline{n}) = 1. \quad (38)$$

As is known to those skilled in the imaging arts, in particular the nuclear medicine arts, a system or apparatus is provided to obtain the projection data or image data of an area or volume being imaged. For example, an x-ray CT scanner typically includes a movable x-ray tube that generates the x-ray beam and a multiplicity of detectors, each positioned at known locations, which receive the x-ray photons.

A computer system including memory, a microprocessor, storage devices, devices for reading computer readable mediums, input devices (e.g., mouse and keyboard) and a display also is communicatively coupled to the detectors to receive the projection data. As described herein, a software program embodying the methodologies of the present invention is executed on such a computer so as to reconstruct images such as cross-sectional images form the acquired projection data. Such a computer system also is embodied in tomography imaging systems such as those described herein (MRI, SPECT, PET) for processing the projection data acquired using such systems. Thus, and as indicated herein, the present invention also features systems embodying such scanners, computer systems and a software program for execution on the computer system that embodies the methods of the present invention.

Although a preferred embodiment of the invention has been described using specific terms, such description is for illustrative purposes only, and it is to be understood that changes and variations may be made without departing from the spirit or scope of the following claims.

Incorporation by Reference

All patents, published patent applications and other references disclosed herein are hereby expressly incorporated by reference in their entireties by reference.

Equivalents

Those skilled in the art will recognize, or be able to ascertain using no more than routine experimentation, many equivalents of the specific embodiments of the invention described herein. Such equivalents are intended to be encompassed by the following claims.

What is claimed is:

1. A method for reconstruction of an image and for compensating for motion of a dynamically deforming object to be imaged by providing a reconstructed image of the object, comprising:
   acquiring projection data of the object using a scanner;
   calculating, by a controller, motion vector field data for the object to estimate a motion of the object;
   reconstructing, by the controller, the acquired projection data utilizing an image reconstruction methodology; and
   generating, by the controller, the reconstructed image based on the reconstructed projection data and the calculated motion vector field data,
   wherein the image reconstruction methodology includes steps of:
   a) defining a region-of-interest (ROI) and a set of Hilbert lines such that every point inside the ROI lies on only one Hilbert line, and all line integral projection data passing through any object point on each Hilbert line are measured,
   b) along each Hilbert line, computing a derivative backprojection to obtain a Hilbert transformed image,
   c) along each Hilbert line, inverting the Hilbert transformed image to obtain a function, and
   d) reconstructing a finite set of images at a reference time using the steps a)-c) to compensate for a time-dependent affine transformation and applying a weighted summation to the finite set of images using the following equation:

$$f_0(x_t) = \sum_{m=1}^{M} W_{0,m}(x_t) f_{0,m}(x_t) \bigg/ \sum_{m=1}^{M} W_{0,m}(x_t),$$

where $f_{o,m}$ is the finite set of images at the reference time, and $W_{o,m}$ is a spatially varying weight which corresponds to spatially changing elements of affine transformation.

2. The method of claim 1, wherein the projection data is acquired using an imaging modality selected from the group consisting of x-ray computerized tomography (CT) scanning, Magnetic Resonance Imaging (MRI) scanning, single-photon emission computed tomography (SPECT), and positron emission tomography (PET).

3. The method of claim 1, further comprising the step of:
   determining projection data from the reconstructed image;
   optimizing the reconstructed image,
   wherein said optimizing includes iteratively comparing the projection data determined from the reconstructed image with the acquired projection data and determining that the reconstructed image is optimal when such comparison shows a convergence of the determined projection data with the acquired projection data.

4. The method of claim 1, wherein an imaging modality of the reconstructed image is a tomographic imaging modality.

5. A non-transitory computer readable medium on which is stored an applications program for execution on a computer; wherein said applications program includes code segments, instruction and criteria for carrying out the method as set forth in claim 1.

6. A method for reconstruction of an image while compensating for motion of a dynamically deforming object to be imaged by reconstructing an image of the object, comprising:
   acquiring projection data of the object using a scanner; and
   executing, by the controller, an image reconstruction methodology to generate the reconstructed image based on the acquired projection data, wherein the image reconstruction methodology includes steps of:
a) defining a region-of-interest (ROI) and a set of Hilbert lines such that every point inside the ROI lies on only one Hilbert line, and all line integral projection data passing through any object point on each Hilbert line are measured,
b) along each Hilbert line, computing a derivative backprojection to obtain a Hilbert transformed image,
c) along each Hilbert line, inverting the Hilbert transformed image to obtain a function, and
d) reconstructing a finite set of images at a reference time using the steps a)-c) to compensate for a time-dependent affine transformation and applying a weighted summation to the finite set of images using the following equation:

$$f_0(x_t) = \sum_{m=1}^{M} W_{0,m}(x_t) f_{0,m}(x_t) \Big/ \sum_{m=1}^{M} W_{0,m}(x_t),$$

where $f_{o,m}$ is the finite set of images at the reference time, and $W_{o,m}$ is a spatially varying weight which corresponds to spatially changing elements of affine transformation.

7. The method of claim 6, wherein the projection data is acquired using an imaging modality selected from the group consisting of x-ray computerized tomography (CT) scanning, Magnetic Resonance Imaging (MRI) scanning, single-photon emission computed tomography (SPECT), and positron emission tomography (PET).

8. The method of claim 6, further comprising the step of:
determining projection data from the reconstructed image;
optimizing the reconstructed image; and
wherein said optimizing includes iteratively comparing the projection data determined from the reconstructed image with the acquired projection data and determining that the reconstructed image is optimal when such comparison shows a convergence of the determined projection data with the acquired projection data.

9. The method of claim 6, wherein an imaging modality of the reconstructed image is a tomographic imaging modality.

10. A non-transitory computer readable medium on which is stored an applications program for execution on a computer; wherein said applications program includes code segments, instruction and criteria for carrying out the method as set forth in claim 6.

11. A tomographic imaging system for imaging a dynamically deforming object and providing an output of a reconstructed image, the imaging system including a computer system including a microprocessor, wherein said system further includes:
a scanner, wherein projection data of the object is acquired using the scanning apparatus; and
a software program for execution on the microprocessor, which when executed cause the microprocessor to:
calculate motion vector field data for the object to estimate a motion of the object,
reconstruct the acquired projection data utilizing an image reconstruction methodology, and
generate the reconstructed image based on the reconstructed projection data and the calculated motion vector field data,
wherein the image reconstruction methodology includes steps of:
a) defining a region-of-interest (ROI) and a set of Hilbert lines such that every point inside the ROI lies on only one Hilbert line, and all line integral projection data passing through any object point on each Hilbert line are measured,
b) along each Hilbert line, computing a derivative backprojection to obtain a Hilbert transformed image,
c) along each Hilbert line, inverting the Hilbert transformed image to obtain a function, and
d) reconstructing a finite set of images at a reference time using the steps a)-c) to compensate for a time-dependent affine transformation and applying a weighted summation to the finite set of images using the following equation:

$$f_0(x_t) = \sum_{m=1}^{M} W_{0,m}(x_t) f_{0,m}(x_t) \Big/ \sum_{m=1}^{M} W_{0,m}(x_t),$$

where $f_{o,m}$ is the finite set of images at the reference time, and $W_{o,m}$ is a spatially varying weight which corresponds to spatially changing elements of affine transformation.

12. A tomographic imaging system for imaging a dynamically deforming object and providing an output of a reconstructed image, the imaging system including a computer system including a microprocessor, wherein said system further includes:
a scanner, wherein projection data of the object is acquired by the scanning apparatus; and
a software program for execution on the microprocessor, which when executed cause the microprocessor to:
execute an image reconstruction methodology to generate the reconstructed image based on the acquired projection data,
wherein the image reconstruction methodology includes steps of:
a) defining a region-of-interest (ROI) and a set of Hilbert lines such that every point inside the ROI lies on only one Hilbert line, and all line integral projection data passing through any object point on each Hilbert line are measured,
b) along each Hilbert line, computing a derivative backprojection to obtain a Hilbert transformed image,
c) along each Hilbert line, inverting the Hilbert transformed image to obtain a function, and
d) reconstructing a finite set of images at a reference time using the steps a)-c) to compensate for a time-dependent affine transformation and applying a weighted summation to the finite set of images using the following equation:

$$f_0(x_t) = \sum_{m=1}^{M} W_{0,m}(x_t) f_{0,m}(x_t) \Big/ \sum_{m=1}^{M} W_{0,m}(x_t),$$

where $f_{o,m}$ is the finite set of images at the reference time, and $W_{o,m}$ is a spatially varying weight which corresponds to spatially changing elements of affine transformation.

* * * * *